(12) United States Patent
Pokorney et al.

(10) Patent No.: US 8,603,122 B2
(45) Date of Patent: Dec. 10, 2013

(54) THROMBUS REMOVAL SYSTEM AND PROCESS

(75) Inventors: James L. Pokorney, Northfield, MN (US); Stephanos Finitsis, Nancy (FR); John Kucharczyk, Reno, NV (US)

(73) Assignee: Nexgen Medical Systems, Incorporated, Davis, CA (US)

( * ) Notice: Subject to any disclaimer, the term of this patent is extended or adjusted under 35 U.S.C. 154(b) by 1520 days.

(21) Appl. No.: 11/974,490

(22) Filed: Oct. 12, 2007

(65) Prior Publication Data
US 2008/0091223 A1 Apr. 17, 2008

Related U.S. Application Data

(63) Continuation-in-part of application No. 11/356,321, filed on Feb. 16, 2006, now Pat. No. 7,955,345, which is a continuation-in-part of application No. 11/097,354, filed on Apr. 1, 2005, now Pat. No. 7,955,344.

(60) Provisional application No. 60/851,699, filed on Oct. 13, 2006.

(51) Int. Cl.
*A61B 17/22* (2006.01)

(52) U.S. Cl.
USPC .......................................... 606/159; 606/200

(58) Field of Classification Search
USPC .................. 606/110, 113, 127, 159, 192, 200
See application file for complete search history.

(56) References Cited

U.S. PATENT DOCUMENTS

| | | | |
|---|---|---|---|
| 3,174,851 A | 3/1965 | Buehler et al. | 148/426 |
| 3,351,463 A | 11/1967 | Rozner et al. | 148/426 |
| 4,448,195 A | 5/1984 | LeVeen et al. | 606/194 |
| 4,827,931 A | 5/1989 | Longmore | 606/148 |
| 4,922,924 A | 5/1990 | Gambale et al. | 600/585 |
| 4,989,608 A | 2/1991 | Ratner | 600/420 |
| 5,064,428 A | 11/1991 | Cope et al. | 606/127 |
| 5,122,136 A | 6/1992 | Guglielmi et al. | 606/32 |
| 5,154,179 A | 10/1992 | Ratner | 600/420 |
| 5,211,166 A | 5/1993 | Sepponen | 600/420 |
| 5,234,437 A | 8/1993 | Sepetka | 606/108 |
| 5,250,071 A | 10/1993 | Palermo | 606/198 |
| 5,261,916 A | 11/1993 | Engelson | 606/108 |
| 5,304,195 A | 4/1994 | Twyford, Jr. et al. | 606/191 |
| 5,312,415 A | 5/1994 | Palermo | 606/108 |
| 5,350,397 A | 9/1994 | Palermo et al. | 606/200 |

(Continued)

*Primary Examiner* — Kathleen Holwerda
*Assistant Examiner* — David Eastwood
(74) *Attorney, Agent, or Firm* — Mark A. Litman & Associates, P.A.

(57) ABSTRACT

A device capable of capturing and facilitating the removal of a thrombus in blood vessels (or stones in biliary or urinary ducts, or foreign bodies) uses a soft coil mesh with the aid of a pull wire or string to engage the surface of a thrombus, and remove the captured thrombus. The soft coil mesh is formed by an elongated microcoil element that forms the helical elements of a macrocoil element. The microcoil element provides a relatively elastic effect to the helical elements forming the macrocoil and allows for control of gripping forces on the thrombus while reducing non-rigid contact of the device with arterial walls. The use of multiple coil mesh elements, delivered through a single lumen or multiple lumens, preferably with separate control of at least one end of each coil, provides a firm grasp on a distal side of a thrombus, assisting in non-disruptive or minimally disrupted removal of the thrombus upon withdrawal of the device.

20 Claims, 20 Drawing Sheets

Device Design

(56) References Cited

U.S. PATENT DOCUMENTS

| | | | |
|---|---|---|---|
| 5,354,295 A | 10/1994 | Guglielmi et al. | 606/32 |
| 5,375,596 A | 12/1994 | Twiss et al. | 600/424 |
| 5,522,819 A | 6/1996 | Graves et al. | 606/113 |
| 5,744,958 A | 4/1998 | Werne | 324/318 |
| 5,772,609 A | 6/1998 | Nguyen et al. | 600/585 |
| 5,851,206 A * | 12/1998 | Guglielmi et al. | 606/28 |
| 5,868,754 A | 2/1999 | Levine et al. | 606/108 |
| 5,895,398 A * | 4/1999 | Wensel et al. | 606/159 |
| 5,919,187 A * | 7/1999 | Guglielmi et al. | 606/32 |
| 5,972,019 A * | 10/1999 | Engelson et al. | 606/200 |
| 6,024,765 A * | 2/2000 | Wallace et al. | 606/191 |
| 6,059,779 A * | 5/2000 | Mills | 606/41 |
| 6,066,149 A * | 5/2000 | Samson et al. | 606/159 |
| 6,066,158 A * | 5/2000 | Engelson et al. | 606/200 |
| 6,139,510 A | 10/2000 | Palermo | 600/585 |
| 6,371,972 B1 * | 4/2002 | Wallace et al. | 606/200 |
| 6,436,112 B2 | 8/2002 | Wensel et al. | 606/159 |
| 6,511,492 B1 | 1/2003 | Rosenbluth et al. | 606/159 |
| 6,805,684 B2 | 10/2004 | Bonnette et al. | 604/22 |
| 2004/0039435 A1 | 2/2004 | Hancock et al. | 623/1.2 |
| 2004/0098023 A1 | 5/2004 | Lee et al. | 606/200 |
| 2004/0138692 A1 | 7/2004 | Phung et al. | 606/200 |
| 2004/0225229 A1 | 11/2004 | Viola | 600/564 |
| 2005/0038447 A1 | 2/2005 | Huffmaster | 606/127 |
| 2008/0125798 A1 * | 5/2008 | Osborne et al. | 606/159 |

* cited by examiner

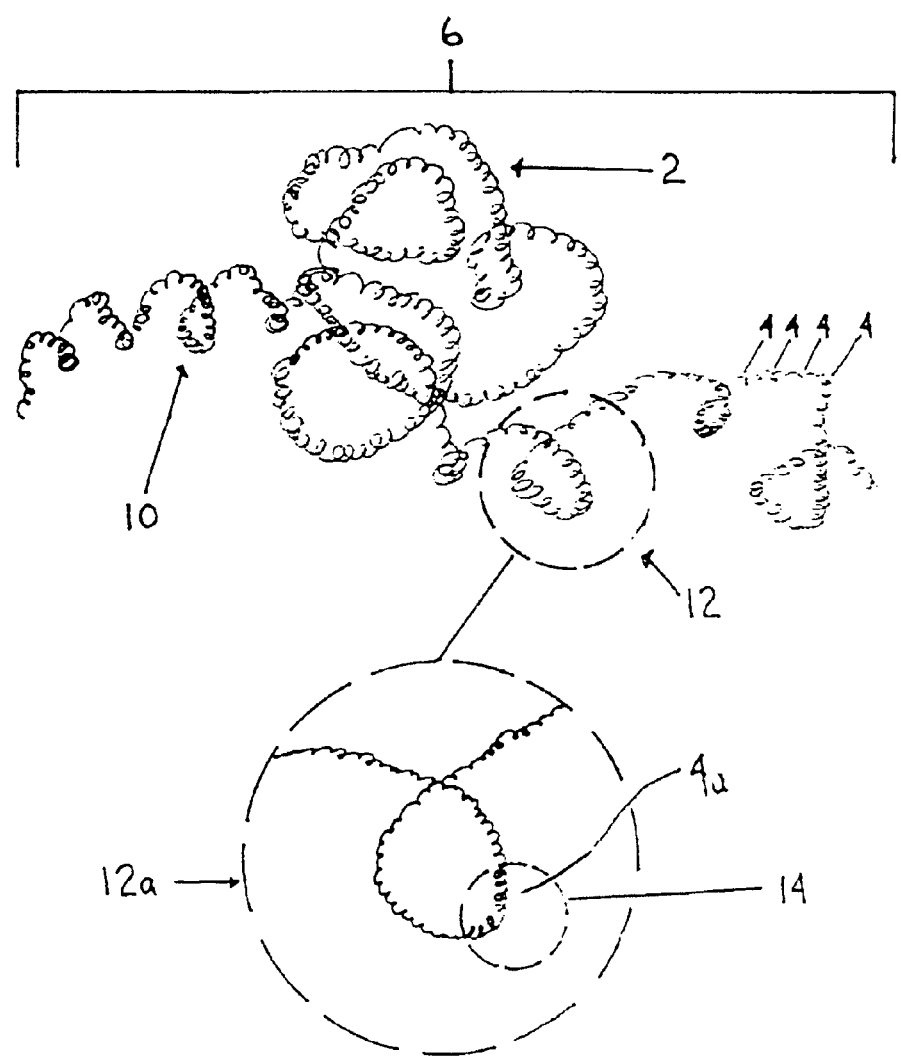

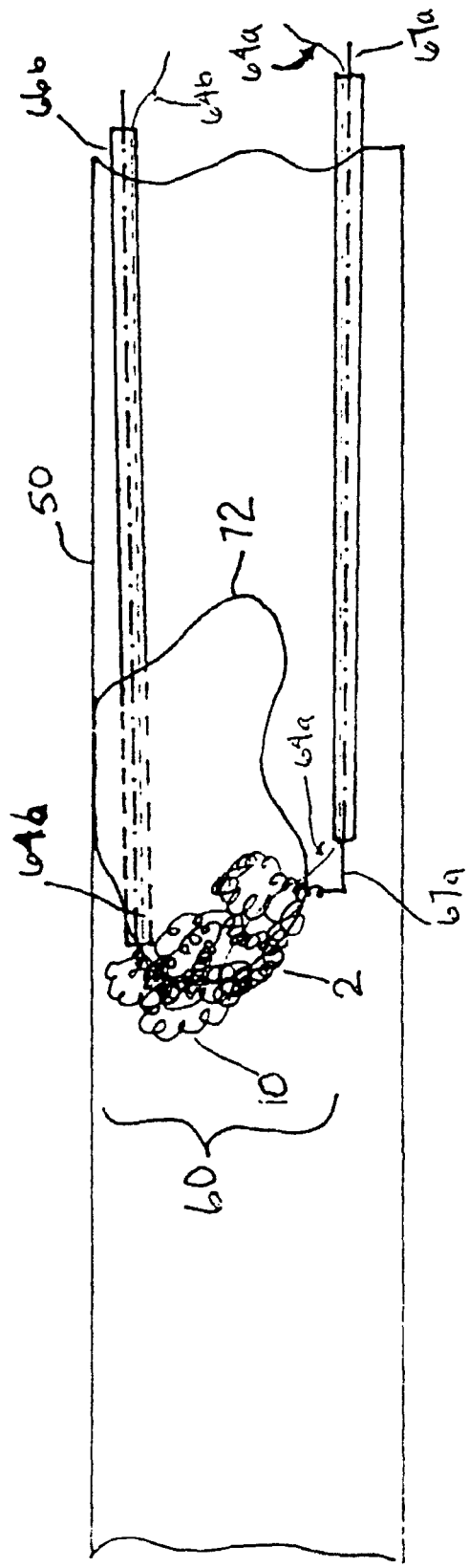

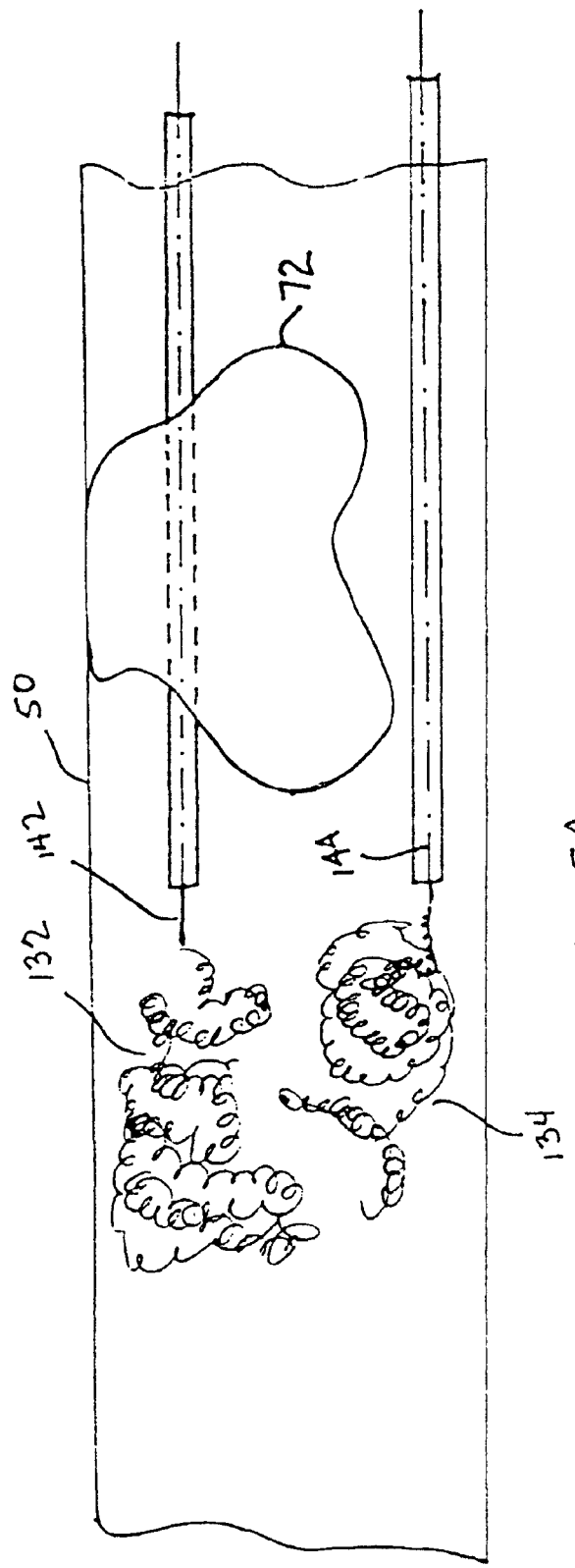

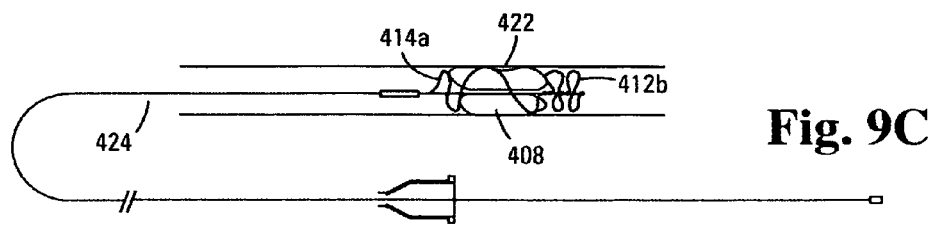
Fig. 9C
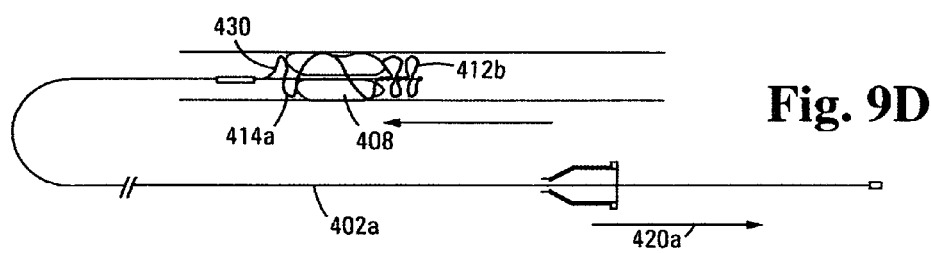
Fig. 9D
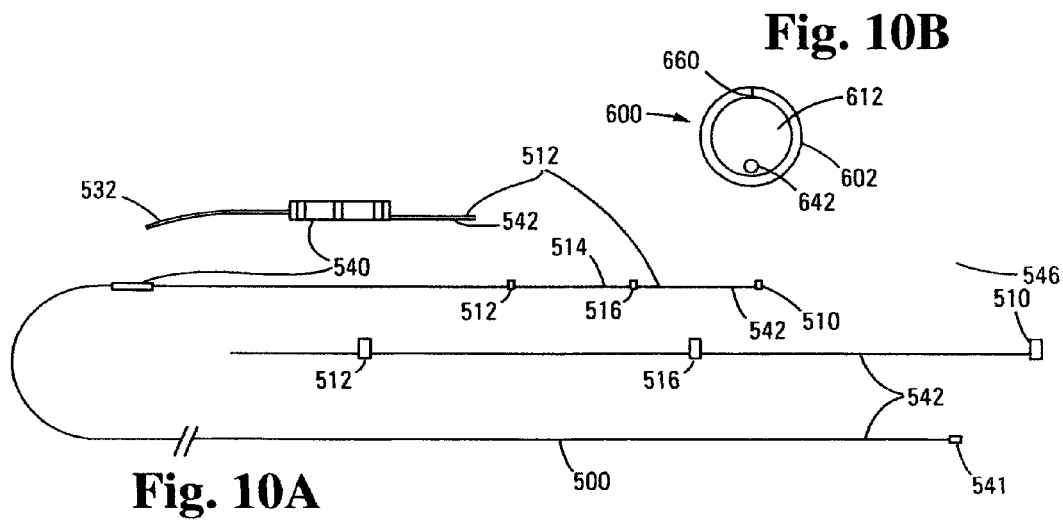
Fig. 10B
Fig. 10A

Figure 11 – Device Design
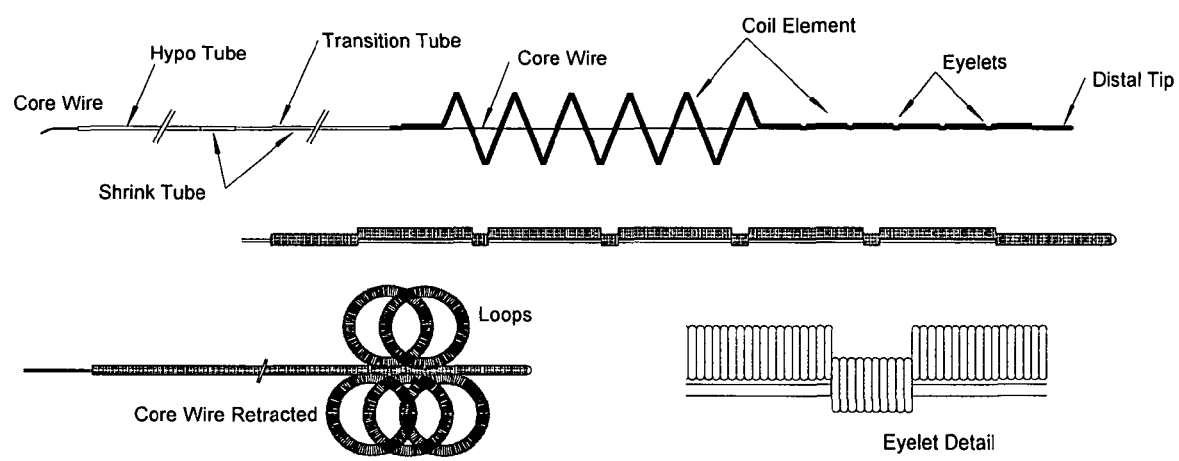

Figure 12 – Principle of Operation
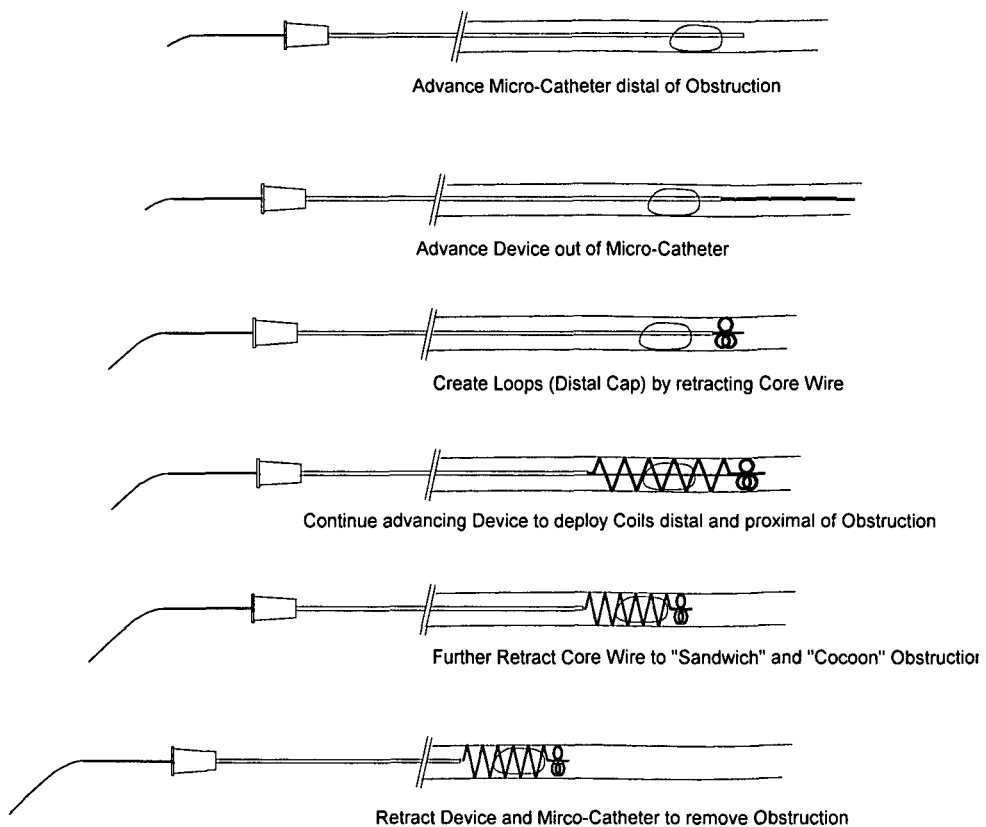

THROMBUS REMOVAL SYSTEM AND PROCESS

RELATED APPLICATION DATA

The present application claims priority from U.S. Provisional Application Ser. No. 60/851,699 filed 13 Oct. 2006 and is a continuation-in-part of U.S. patent application Ser. No. 11/356,321 filed 16 Feb. 2006 now U.S. Pat. No. 7,955,345, which is in turn a continuation-in-part of U.S. patent application Ser. No. 11/097,354, filed 1 Apr. 2005 now U.S. Pat. No. 7,955,344.

BACKGROUND OF THE INVENTION

1. Field of the Invention

The present invention pertains to intravascular medical devices. More particularly, the present invention pertains to devices for isolating, capturing, and removing blood clots from a blood vessel. This same system may also be used to safely and effectively retrieve obstructions, such as coils, balloons, or catheter fragments dislodged during interventional procedures, from the blood stream. The same system may further be used to remove obstructions from ducts and other cavities of the body, such as, for example, foreign bodies or stones from the urinary or the biliary tracts.

2. Background of the Art

The present invention pertains generally to thrombus collection and removal. The process of thrombosis may produce a clot in a patient's vasculature. Such clots may occasionally be harmlessly dissolved in the blood stream. At other times, however, such clots may lodge in a blood vessel or embolize to a distal blood vessel where they can partially or completely occlude the flow of blood. If the partially or completely occluded vessel provides blood to sensitive tissue such as the brain or heart, for example, serious tissue damage may result.

When symptoms of vascular occlusion are apparent, such as an occlusion resulting in a stroke, immediate intervention is required to minimize tissue damage. One approach is to treat a patient with clot dissolving drugs, such as recombinant tissue plasminogen activator, streptokinase, or heparin. These drugs, however, do not immediately dissolve the blood clot and generally are useful only when administered within a short time period after onset of stroke symptoms.

Published U.S. Patent Application 2005/0038447 describes A medical device for removing clots from a blood vessel, comprising: a first longitudinally-oriented spine having a distal end; a pushing member coupled to the proximal end of the first longitudinally-oriented spine and extending proximally therefrom; and a clot-grabbing basket generally disposed between and coupled to the first longitudinally-oriented spine.

Published U.S. Patent Application 2004/0138692 discloses an embolus extractor, comprising: an elongated shaft having a proximal end and a distal end; first and second struts, each strut having a proximal end and a distal end coupled to the distal end of the shaft; the first and second struts having a first position and a second position, wherein in the first position, the distal ends and the proximal ends of the struts are spaced at a first distance, and in the second position the distal ends and the proximal ends of the struts are spaced at a second distance, the second distance being less than the first distance; and third and fourth struts, each strut coupled to one of the first and second struts via a proximal end and distal end.

Published U.S. Patent Application 2004/0098023 discloses a vasoocclusive device, comprising: a core member; and a fibrous structure carried by the core member, the fibrous structure comprises one or more strands of nanofibers. The vasoocclusive device may provide the fibrous structure in a product generated at least in part by an electrospinning process comprises the steps of: supplying a polymer solution through a needle; electrostatically charging the needle; electrostatically charging a metal plate that is placed at a distance from the needle, the metal plate having a charge that is opposite that of the needle, thereby sending a jet of the polymer solution towards the metal plate; and collecting the fibrous structure from the metal plate.

Published U.S. Patent Application 2004/0039435 discloses a self-expanding, pseudo-braided device embodying a high expansion ratio and flexibility as well as comformability and improved radial force. The pseudo-braided device is particularly suited for advancement through and deployment within highly tortuous and very distal vasculature. Various forms of the pseudo-braided device are adapted for the repair of aneurysms and stenoses as well as for use in thrombectomies and embolic protection therapy.

There are a variety of ways of discharging shaped coils and linear coils into a body cavity. In addition to those patents that describe physically pushing a coil out of the catheter into the body cavity (e.g., Ritchart et al.), there are a number of other ways to release the coil at a specifically chosen time and site. U.S. Pat. No. 5,354,295 and its parent, U.S. Pat. No. 5,122,136, both to Guglielmi et al., describe an electrolytically detachable embolic device.

A variety of mechanically detachable devices are also known. Various examples of these devices are described in U.S. Pat. No. 5,234,437, to Sepetka, U.S. Pat. No. 5,250,071 to Palermo, U.S. Pat. No. 5,261,916, to Engelson, U.S. Pat. No. 5,304,195, to Twyford et al., U.S. Pat. No. 5,312,415, to Palermo, and U.S. Pat. No. 5,350,397, to Palermo et al.

Various configurations have been used to remove calculi from the biliary or urinary system. See, for instance, U.S. Pat. No. 5,064,428. Additionally, devices having various configurations have been used to remove objects from the vasculature. For example, surgical devices comprising one or more expandable and collapsible baskets have been described for removing or piercing a thrombus in the vasculature. See, U.S. Pat. No. 6,066,149. U.S. Pat. No. 5,868,754 describes a three prong-shaped device for capturing and removing bodies or articles from within a vessel.

U.S. Pat. Nos. 5,895,398 and 6,436,112 to Wensel disclose a clot and foreign body removal device comprising a clot capture coil connected to an insertion mandrel within a catheter. The clot capture coil disclosed by Wensel is made out of a material with shape memory which allows it to be deformed within the catheter and then reformed to its original coil configuration when the coil is moved outside of the catheter lumen. The Wensel invention also provides for a biphasic coil which changes shape upon heating or passing an electric current, wherein the coil can be used to ensnare and corkscrew a clot in a vessel, which is then extracted from the vessel by moving the clot capture coil and catheter proximally until the clot can be removed. According to the Wensel invention, foreign bodies are similarly captured by deploying the coil distal to the foreign body and moving the clot capture coil proximally until the foreign body is trapped within the coil Published U.S. Patent Application 2004/0225229 describes a device comprising a core wire having a distal end and a proximal end; a catheter shaft having a proximal catheter end, a distal catheter end and a lumen through which the core wire is passed such that the distal end of the core wire extends beyond the distal catheter end; a retrieval element disposed at the distal end of the core wire, the retrieval element movable from a radially contracted position to a radially expanded position; and a first stop element attached to the core wire, the first stop element configured to prevent overexpansion of the retrieval element.

Among commercial thrombus-removal systems are at least the following:

1) The MERCI system of Concentric Medical that has a form of a corkscrew or helix spring. In this system, which may use a large 0.018 F microcatheter, the microcatheter tip is first positioned across the thrombus with the help of a guidewire after which the guidewire is exchanged with the system which is deployed distal and into the thrombus. The corkscrew shape of the device facilitates penetration into the thrombus. The thrombus can then be retrieved from the artery into a large 9 French guiding catheter, and removed from the patient's body.
2) The In-Time system of Boston Scientific resembles a clam-shell when compressed, but once the microcatheter is placed through the thrombus and the device extended out of the microcatheter, it expands into 4 strings that form an oval, as with a rugby football. The system is then pulled back to engage and remove the thrombus from the blood vessel. This is similar to the disclosed structure in Published US Application 2004/0138692.
3) Another system, known in the trade as a "lasso" is basically a simple catheter with a wire attached to its end. The wire makes a loop and enters back into the catheter (e.g., a large 0.018 F microcatheter). The operator changes the aspect of the loop by pulling on the wire. This system was originally conceived to catch foreign bodies.
4) The Catch system of Balt is a stent closed on one end forming a basket that is deployed distal to the thrombus. The operator then pulls the system and retrieves the thrombus. This is similar to the structure in FIG. 7 of U.S. Pat. No. 6,805,684.

The above systems may have various practical and cost disadvantages. Although several of the commercial systems are designed to penetrate clot, this may in fact be impossible if the clot is made up of firm fibrin. The device may therefore not penetrate the clot but instead will slide over the thrombus. The process of engagement and retraction of a thrombus may also fractionate the clot, producing distal embolization. Currently available systems can also be difficult to guide or deploy at the site of the thrombus, or may be traumatic to the artery, and some systems are quite expensive. In addition, all these systems are bulky and cannot be safely and effectively used in small caliber blood vessels. All references cited herein are incorporate by reference in their entirety for the content of their disclosure.

SUMMARY OF THE INVENTION

A device capable of isolating, capturing, and facilitating the removal of a thrombus in blood vessels (or stones in biliary or urinary ducts, or foreign bodies) uses a soft coil mesh with the aid of a pull wire to engage the surface of a thrombus, and remove the captured thrombus. The mechanical thrombectomy device is positioned by MRI or angiography guided percutaneous transluminal catheter delivery within the lumen of the blood vessel directly adjacent to the thrombus. The soft coil mesh is formed by an elongated microcoil element that forms the helical elements of a macrocoil element having an adjustable stiffness which provides reliable dynamic compliance matching with the viscoelastic properties of the thrombus undergoing removal. The microcoil elements further provide a relatively elastic effect to the helical element forming the macrocoil that allows for control of gripping forces on the thrombus while reducing non-rigid circumferential contact of the device with vessel endoluminal surfaces. The use of multiple coil mesh elements, delivered through a single lumen or multiple lumen catheters, preferably with separate control of at least one end of each coil, provides a firm grasp on a distal side of a thrombus, facilitating non-disruptive or minimally disruptive removal of the thrombus upon withdrawal of the device.

One aspect of the present invention is to provide a mechanical thrombectomy system that can reliably and safely navigate tortuous blood vessels to the site of an intracranial or extracranial thrombus.

A second aspect of the present invention is to provide a mechanical thrombectomy device that can reliably and securely entrap a soft or hard thrombus without fragmenting the thrombus or damaging the intima of the blood vessel.

A third aspect of this invention is to provide a mechanical thrombectomy device that is biocompatible, visible on both X-ray and MR imaging, and compatible with standard medical catheters.

A further aspect of this invention is to provide a mechanical thrombectomy device that can safely and completely remove thrombus of any density from any blood vessel in the human body.

A still further aspect of the invention is the provision of a single macrocoil that may be displaced from a carrier on the distal and proximal sides of a thrombus to engage the thrombus from the distal and proximal sides, respectively.

Another further aspect of the invention is the provision of multiple macrocoils that may be separately displaced from a carrier on the proximal and the distal sides of the thrombus to engage the thrombus from the proximal and distal sides, respectively.

Another further aspect of the invention is the provision of a macrocoil that may be displaced from a carrier on the distal side of a thrombus and a separate thrombus support that may be positioned the proximal side of the thrombus to engage the thrombus from both the distal and proximal sides.

A still further aspect of the present invention is the provision of eyelets that may be displaced on the distal side of the thrombus to facilitate engagement of the thrombus using the macrocoil.

BRIEF DESCRIPTION OF THE FIGURES

FIG. 1 shows a structural material 2 that can be used as a soft coil capture element.

FIG. 2B shows the meshwork of the capture device in close contact with the distal portion of a thrombus within an artery.

FIG. 5A shows the capture device in a format of providing two distinct macrocoil/microcoil systems.

FIG. 9C shows the displacement of a cannula/coil on the proximal side of the thrombus after the formation of the more complex coil shape in FIG. 9B.

FIG. 9D shows the retraction of the device after the cannula/coil on the proximal side of the thrombus has been achieved, thus removing the clot while supported on both the distal and proximal sides of the thrombus.

FIG. 10A shows a assembly drawing with separately magnified device components for better definition.

FIG. 10B shows a cross-section of a portion of the device of FIG. 10A near an eyelet.

FIG. 11 is a sketch of the Device design showing a platinum coil element attached to a stainless steel hypo tube via a polyimide transition tube. Within the tubes and coil element is a stainless steel core wire. A protective shrink tube covers the transition tube and the distal end of the hypo tube. Eyelets in the coil elements, the distal tip of the coil elements and the core wire are also shown.

FIG. 12 illustrates the general principle of operation of the present technology. The Device is inserted into a microcatheter that is already placed distal of the obstruction. The Device is advanced and then actuated to form the distal Loops which act as a cap. To ensure retrieval, the pre-shaped coils are advanced out of the microcatheter. These coils are placed both distal and proximal of the obstruction. Once placed, the core wire is further retracted to tighten the coil structure around the obstruction. The obstruction, now fully sandwiched or cocooned within the coil element, can be safely removed.

DETAILED DESCRIPTION OF THE INVENTION

Figure 1A:
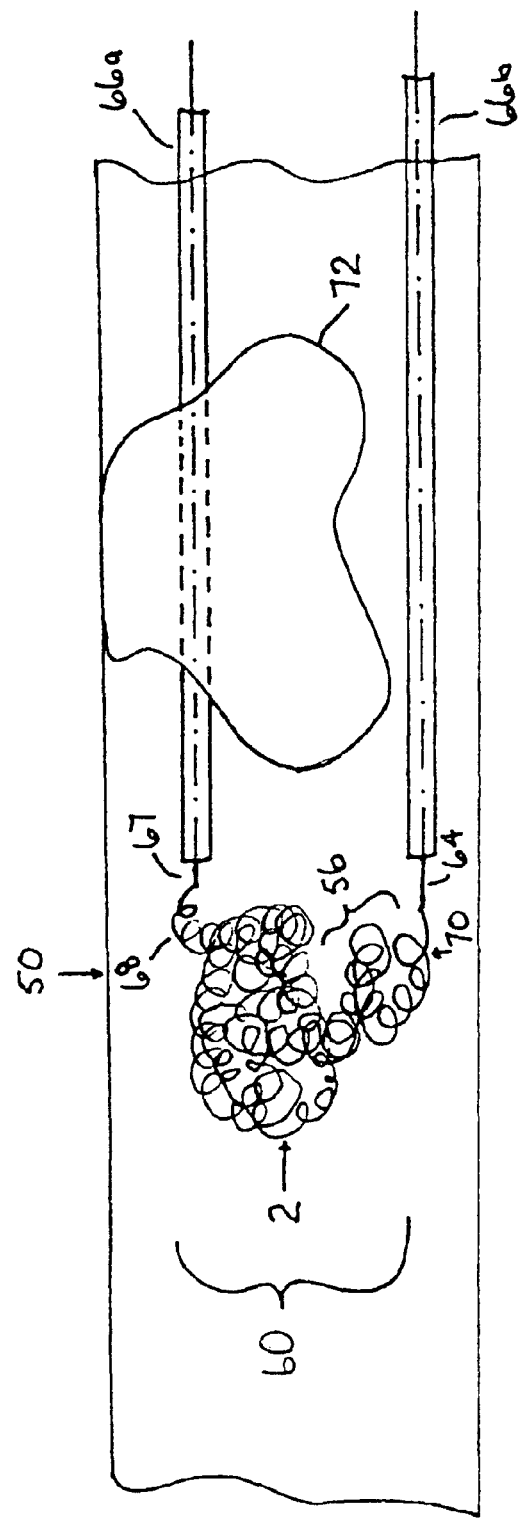
FIG. 1A shows the microcoil/macrocoil structure of the soft coil capture device described herein.

The following description should be read with reference to the drawings wherein like reference numerals indicate like elements throughout the several views. The detailed description and drawings illustrate example non-limiting specific embodiments of the generic claimed invention.

FIG. 1 shows a structural material 2 that can be used as a soft coil capture element in the practice of the technology described herein. The material 2 has microcoils or microloops forming a continuing chain 6 of microcoils that form the macrocoil or macrohelix 10. The term 'microcoil' as used herein should not be confused with the RF or MRI responsive coils or microcoils that are used in the medical imaging art. The microcoils of the present invention are small coils compared to the macrocoils 10 which are large coils. The microcoils are made from the structural material (such as metal, polymeric or composite filament or wire) that forms the filaments, threads, fibers, or the like that are used to provide the microcoils that build into the macrocoils. The benefits of this material and the structure in which they perform will become apparent from the discussion herein.

The microcoils add a significant degree of dynamic compliance, effective elasticity, structural support and cushioning ability to the macrocoils. The microcoils elongate to give radial and circumferential elasticity to the material 2, without providing hard and large abrasive surfaces that might damage adjacent endoluminal surfaces of the blood vessels undergoing therapy, as would traditional coil or mesh structures.

Figure 1B:
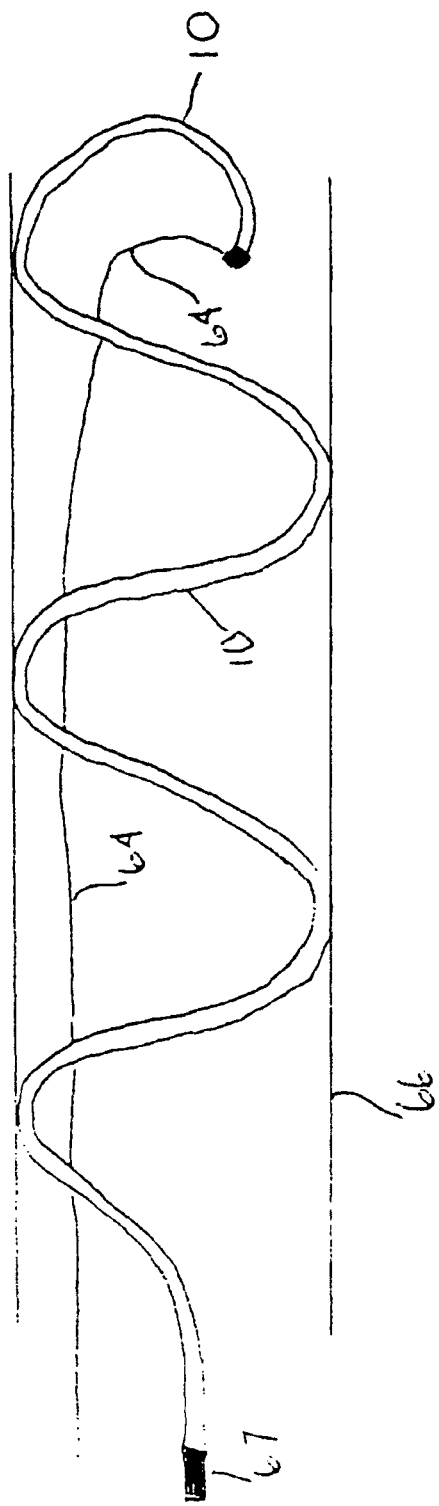
FIG. 1B shows the macrocoil loops constrained in a microcatheter, with a pull string attached to the distal tip of the macrocoil assembly which extends out of the microcatheter, and a pusher wire attached to the proximal end of the macrocoil assembly.

FIG. 1B shows the attachment of the pull string 64 on the distal aspect of the macrocoil complex 10, and the attachment of the pusher (insertion) wire 67 on the proximal aspect of the macrocoil complex 10. The entire macrocoil complex 10 is constrained within the microcatheter 66.

Figure 2:
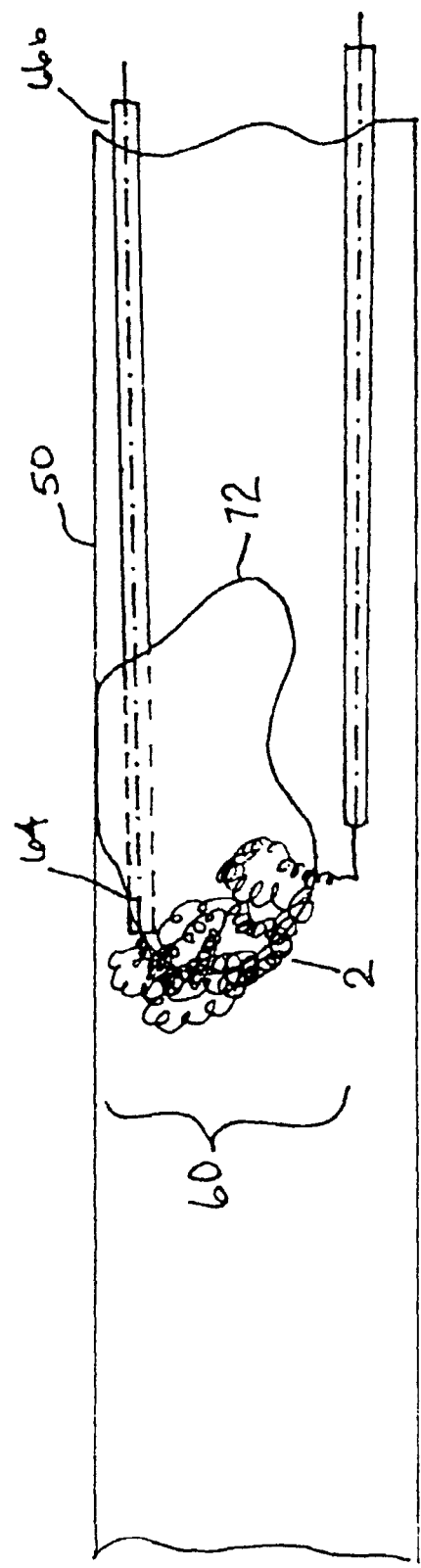
FIG. 2 shows a side view of a general principle of operation for systems according to the present technology.
Figure 2A:
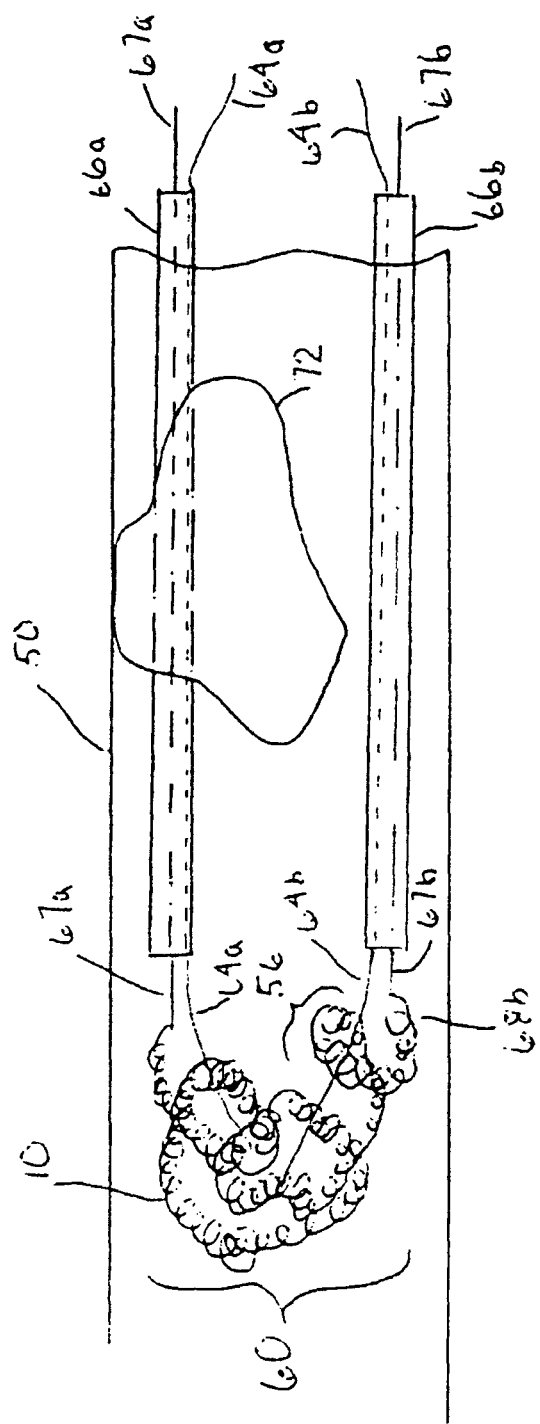
FIG. 2A shows the deployment of two separate microcatheters, each with a separate macrocoil mesh element, each macrocoil mesh element having separate end controls extending from each microcatheter. The two mesh elements are shown integrating on a distal side of a thrombus.

FIG. 2A shows the soft coil material 10 within an artery 50. The macrocoils 56 are shown with the entire length of the coil section 60 of the device being deployed in a slightly extended position beyond the thrombus 72. The pusher wires 67a and 67b stabilize the insertion ends 68a and 68b of the soft coil material 10. The push wires 67a and 67b tend to be thicker than the pull wires 64a and 64b as a matter of course, but they may be designed to be of the same or similar thicknesses, and the pull wires may be thicker than the push wires 67a and 67b.

FIG. 2B shows the capture device 60 in an insertion position in initial contact with the distal portion of a thrombus 72 within an artery 50. A push wire 67b is shown in an exaggerated position, extending beyond its delivery microcatheter 66b. It is not necessary for the push (insertion) wire 67b to itself exit the microcatheter 66b, but only that it move so far forward as to assist the expulsion or deployment of the macrocoil material 10. The retraction wire or retraction string 64b has been shown in a position where it has pulled the material 10 into more intimate contact with the thrombus 72, with the two microcatheters 66a and 66b being themselves somewhat withdrawn from a position previously distal to the thrombus 72.

Figure 3:
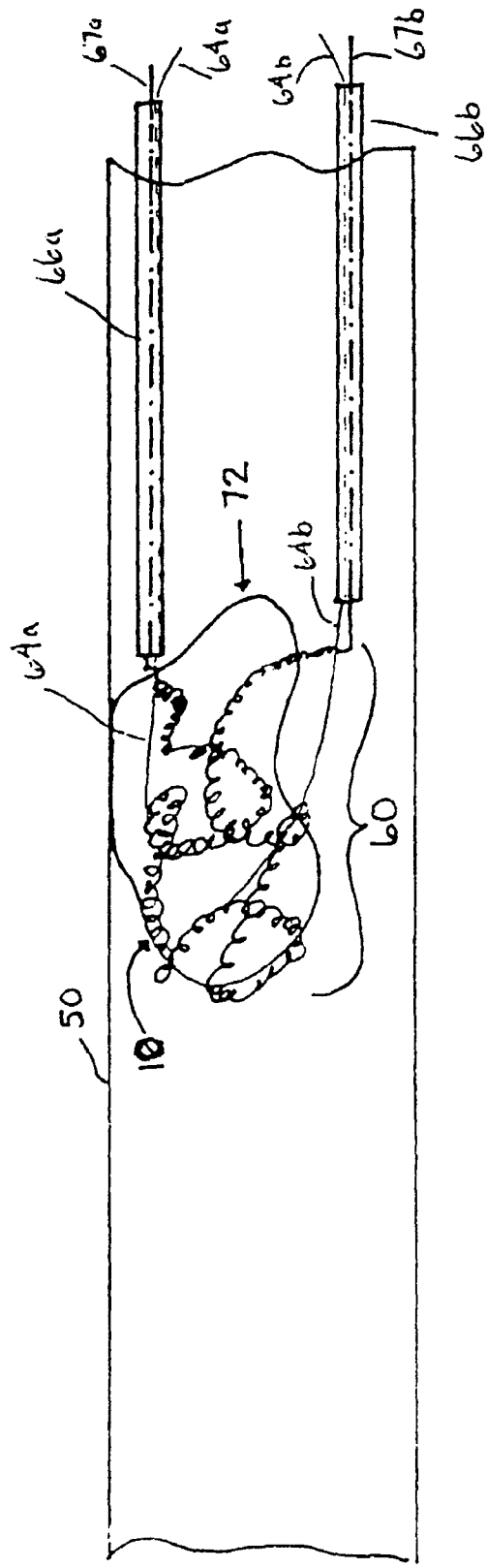
FIG. 3 shows the capture device in a more extensively associated thrombus engaging position during the progression of the soft coil delivery.

FIG. 3 shows a first mode of delivery of the system wherein the microcatheters 66a and 66b have been pulled past the thrombus 72 and then retracted, and the push wires 67a and 67b has been slightly extended beyond the microcatheters 66a and 66b (for illustrative and not essential purposes). The pulling wire 64b and the push wire 67b are sufficiently close together so that the entire length of the extended coil 60 is restrained, but the extended and somewhat retracted coil 60 encircles the major mass of the thrombus 72. The end of the pulling wires 64a and 64b have been retracted to pull the soft coil material 10 into a tangled engagement with the thrombus, engaging the thrombus 72 so that withdrawal of the microcatheter and the four wires 64a, 64b, 67a, and 67b will withdraw the thrombus 72 while enmeshed in the soft coil material. The entire enmeshing length 60 of the soft coil securely entrains the thrombus 72, and the soft coil material 10 assists in reducing breakage of the thrombus 72 and damage to the vascular walls.

Figure 4A:
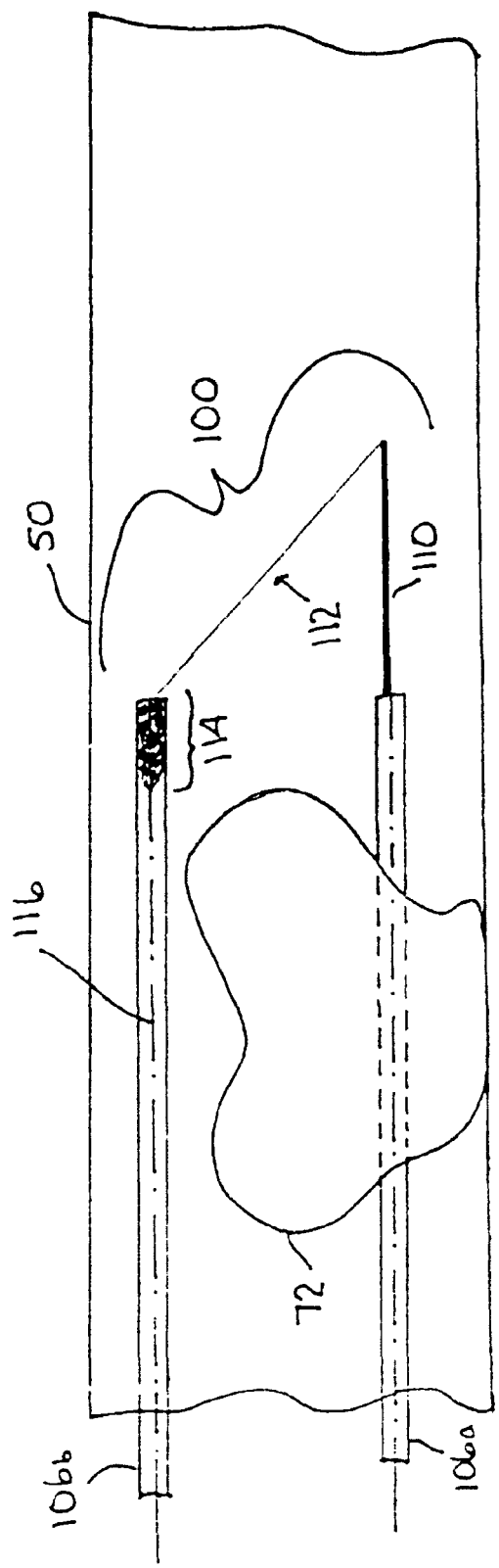
FIG. 4A shows the capture device in a pre-capture position within an artery in a second mode of soft coil delivery, with the coil within a first microcatheter and an extraction wire or extraction string provided from a second microcatheter.

FIG. 4A shows the system 100 delivered in a second delivery mode, with the microcatheters 106a and 106b passing the thrombus 72 mass. There is no push wire in this construction. Rather, there is a pull wire 112 deployed from microcatheter 106a so that the pull wire 112 is positioned in front of the restrained soft coil material 114 even while it is relatively in front of the thrombus 72. The insertion microcatheter has positioned an insertion or support element 110 which has been extended from the microcatheter 106a to deploy the soft coil material support element 114.

Figure 4B:
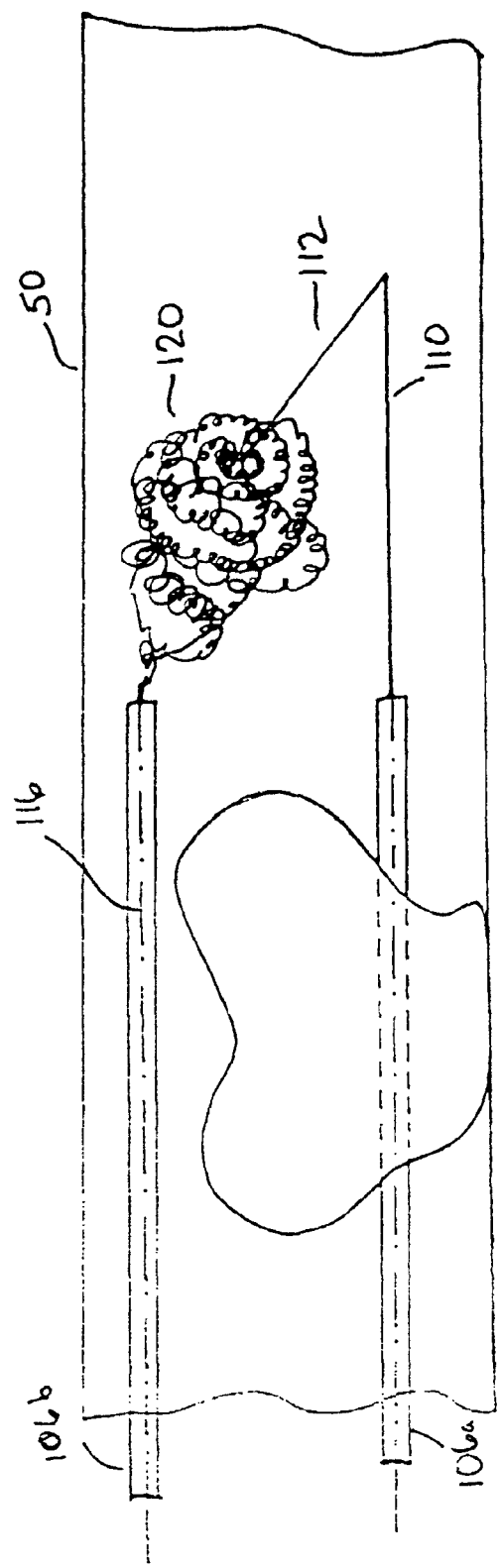
FIG. 4B shows the capture device of FIG. 4A with the macrocoil/microcoil element in a deployed position within an artery.

FIG. 4B shows that the pulling wire 112 has been extended (or retracted) slightly, causing the soft coil material 120 to deploy beyond the thrombus 72 and not yet enmesh the thrombus 72 within the soft coil material 120. By withdrawing the microcatheters 106a and/or 106b, and the two wires 116 and 110, the thrombus 72 can be first secured by the mesh 120 and then withdrawn from the vessel 50 with minimal damage to the vessel 50 and reduced breakage in the thrombus 72. The nature of the mixture of the microcoils and macrocoils causes a constriction of the material around the thrombus, without segmenting (cutting) the thrombus easily, and without providing a cage surface that is as potentially damaging to arterial walls as are other structures used for thrombus retrieval and capture.

The system is made of a 3D soft coil such that when the system gets deployed, it has the tendency to form a three dimensional mesh, with loops of macrocoils extending across the inner lumen of the blood vessel to assure that loops will be able to engage a thrombus when the loops are retracted. The ends of the coils may be attached on either its proximal end to a pusher wire and to its distal end to a very fine pull wire or visa versa. The entire system may be in a very thin format (although the size may vary depending upon the need for fit within particular arterial passages), and can fit into a 0.010 inch inner diameter microcatheter or smaller. Both the pusher wire attached to the macrocoils and the pull wire exit at the proximal end of the microcatheter and can be manipulated by the operator. First the microcatheter is positioned past the thrombus with the help of a microguidewire, preferably between the thrombus and the inner wall of the blood vessel. Once the distal end of the microcatheter lies beyond the thrombus (usually while it is in a distended state, fairly elongate and narrow), the microguidewire is exchanged for the thrombus retrieval system. The thrombus retrieval system is activated and deployed so that a significant portion of the entire length of coil (e.g., ⅕, ¼ or one-third of the coil) is positioned distal to the thrombus. A remaining significant portion of the coil (using, by way of non-limiting examples of amounts, with one-third distal to or past the thrombus), such as at least ⅕, at least ¼ or one-third or more of the coil length is wrapped around or co-distant with the thrombus and ¼, ⅕ or one third or more is placed proximal to the thrombus. Once the coil is deployed with a significant portion at least at the distal end of the thrombus and more desirably a significant portion past the distal end of the thrombus, the operator pulls the thin distal pull wire, so that the mesh of coil loops that has formed around the thrombus or expanded beyond the thrombus retracts on itself and grabs securely the thrombus. The thrombus now can be pulled out of the artery by pulling the microcatheter, the pusher wire and the thin distal wire at the same time out of the artery.

Other advantages of the system (in addition to what has been described already) are its very small size so it can retrieve thrombus from very small arteries, its capacity to pull out the thrombus in one piece, and its softness, allowing manipulation without trauma to the vessel wall. Larger versions have the advantage of retrieving a very large thrombus in one piece. This system may be used in any vessel of the body for the retrieval of thrombus or other material like foreign bodies.

The distal end of the soft coil material (where the pulling wire is attached) may be limited in its ability to extend away from the proximal end of the soft coil material (where the push wire is attached) by using an internal connector, such as a thread, that attaches to both ends of the soft coil, and provides a physical limit to how far the coil may be distended.

Whatever the consistency of the clot, i.e., soft or hard, once the microcatheter has passed the clot, the distal mesh of coils when deployed will form a tight cap that should bring back at least a large part of the thrombus. The loops of the coil that surround the thrombus, producing a cocoon, will prevent the loss of parts of the thrombus if it breaks into pieces. The tendency of the system to break soft thrombus will depend on characteristics such as the soft coil material thickness, the microcoil thickness, the macrocoil thickness, density of the macrocoil, the 3D configuration of the macrocoils and the loop diameter of the coil. Even in the worst case envisioned, one could only deploy a distal and a proximal mesh or use a flow reversing system such as that in the MERCI system.

The pull wire functions to pull the distal tip of the macrocoil to facilitate the formation of a knot. If two macrocoils are used, a pull wire attached to each facilitates the formation of an even better knot. These knots are important to prevent the slippage of the macrocoils from the distal aspect of the thrombus during the removal process. After the macrocoils have been wound around the midportion and proximal aspects of the thrombus, the pull string is used to tighten the entire mesh network.

For a number of reasons, it may be desirable to capture and/or remove clots from the vasculature. The blood vessel can be essentially any vessel or even a duct of the urinary or biliary tracts. The device may include two or more longitudinal wires, for example a guidewire, a push wire and a pull wire, as well as other functional wires (e.g., conductive wires for other features provided with the device, such as a resistive wire to enable heating of the coils, if conductive/resistive. The basket member or region of soft coils is attached to or otherwise coupled with the wires. In general, the device (wires and soft coil material) can be advanced through the vasculature to a suitable location, for example past or adjacent to a clot, and expanded (when past or adjacent to the clot), so that the clot may be captured in the soft coils, upon operator action, and the captured clot can be removed from the vasculature.

The device may be configured to shift between a first generally collapsed configuration and a second generally expanded configuration, especially by the elastic memory of the coil material, and the guidance imposed by the at least two wires. In at least some embodiments, shifting between these configurations includes the longitudinal movement of one or both of the wires relative to one another. Movement of the wires may occur in either the proximal or distal direction and, in the case of both wires moving, may be in the same or opposite directions. Shifting may also result in one or both of the wires moving somewhat laterally (especially with distally controlled wires on the coil material (e.g., with materials that bend when heated, or the like, and a heating element attached thereto) so that the wires become closer or move apart from one another.

Shifting between the collapsed and expanded configurations may occur in a number of differing manners. For example, the device or portions thereof may be made of a shape-memory material (such as nickel-titanium alloy or oriented coils) that can assume a pre-defined shape when unconstrained or when subjected to particular thermal conditions. According to this embodiment, the device can be manufactured to be "self-expanding" (when the longitudinal distension and restraint by the wires is removed) so that it can be delivered in a collapsed configuration, then shift to the expanded configuration when a constraint is removed (e.g., the distal ends of the two wires brought closer together) or when the device is subject to the natural thermal conditions within the blood vessel. Alternatively, shifting may occur by mechanically moving one or both of wires. Moving the wires may occur in a number of different ways such as by moving one or other of the wires attached to the distal or proximal end of the coil material on the device.

As described above, all or portions of the device (including but not limited to the coil materials and the wires) may be manufactured from polymeric, metallic, natural (e.g., gut wires), synthetic, or composite materials. Preferred materials tend to be polymeric, metallic, composite or mixtures or combinations of these materials. A conventional medical structural material such as nickel titanium alloy may be employed. However, any suitable material may be used including metals, metal alloys, polymers, etc. Some examples of suitable metals and metal alloys include stainless steel, such as 304V, 304L, and 316L stainless steel; linear-elastic or super-elastic nitinol or other nickel-titanium alloys, nickel-chromium alloy, nickel-chromium-iron alloy, cobalt alloy, tungsten or tungsten alloys, MP35-N (having a composition of about 35% Ni, 35% Co, 20% Cr, 9.75% Mo, a maximum 1% Fe, a maximum 1% Ti, a maximum 0.25% C, a maximum 0.15% Mn, and a maximum 0.15% Si), hastelloy, monel 400, inconel 825, or the like; or other suitable material.

Some examples of suitable polymers may include polytetrafluoroethylene (PTFE), ethylene tetrafluoroethylene (ETFE), fluorinated ethylene propylene (FEP), polyoxymethylene (POM), polybutylene terephthalate (PBT), polyether block ester, polyurethane, polypropylene (PP), polyvinylchloride (PVC), polyether-ester (for example a polyether-ester elastomer such as ARNITEL® available from DSM Engineering Plastics), polyester (for example a polyester elastomer such as HYTREL® available from DuPont), polyamide (for example, DURETHAN® available from Bayer or CRISTAMID® available from Elf Atochem), elastomeric polyamides, block polyamide/ethers, polyether block amide (PEBA, for example available under the trade name PEBAX®), silicones, polyethylene (PE), Marlex high-density polyethylene, Marlex low-density polyethylene, linear low density polyethylene (for example REXELL®), polyethylene terephthalate (PET), polyetheretherketone (PEEK), polyimide (PI), polyetherimide (PEI), polyphenylene sulfide (PPS), polyphenylene oxide (PPO), polysulfone, nylon, perfluoro(propyl vinyl ether) (PFA), other suitable materials, or mixtures, combinations, copolymers thereof, polymer/metal composites, and the like. In some embodiments, portions of or all of the device can be blended with a liquid crystal polymer (LCP). For example, the mixture can contain up to about 5% LCP.

In some embodiments, a coating, for example a lubricious, a hydrophilic, a protective, or other type of coating may be applied over portions or the entire device. Hydrophobic coatings such as fluoropolymers provide a dry lubricity which improves device exchanges. Lubricious coatings improve steerability and improve lesion crossing capability. Suitable lubricious polymers are well known in the art and may include silicone and the like, hydrophilic polymers such as polyarylene oxides, polyvinylpyrolidones, polyvinylalcohols, hydroxy alkyl cellulosics, algins, saccharides, caprolactones, and the like, and mixtures and combinations thereof. Hydrophilic polymers may be blended among themselves or with formulated amounts of water insoluble compounds (including some polymers) to yield coatings with suitable lubricity, bonding, and solubility. Some other examples of such coatings and materials and methods used to create such coatings can be found in U.S. Pat. Nos. 6,139,510 and 5,772,609, which are incorporated herein by reference. In some embodiments, the sheath or coating may be applied over basket region. This may provide extra surface area to contain clots that might be captured therein.

The sheath or polymeric layer coating may be formed, for example, by coating, electrophoresis, by extrusion, co-extrusion, interrupted layer co-extrusion (ILC), or fusing several segments end-to-end. The layer may have a uniform stiffness or a gradual reduction in stiffness from the proximal end to the distal end thereof. The gradual reduction in stiffness may be continuous as by ILC or may be stepped as by fusing together separate extruded tubular segments. The outer layer may be impregnated with a radiopaque filler material to facilitate radiographic visualization. Those skilled in the art will recognize that these materials can vary widely without deviating from the scope of the present invention.

The device, or portions thereof, may also be coated, plated, wrapped or surrounded by, doped with, or otherwise include a radiopaque material. For example, the wires or coils may be made from a radiopaque material or may include a radiopaque marker member or coil coupled thereto. Radiopaque materials are understood to be materials capable of producing a relatively bright image on a fluoroscopy screen or another imaging technique during a medical procedure. This relatively bright image aids the user of the device in determining its location. Some examples of radiopaque materials can include, but are not limited to, gold, platinum, palladium, tantalum, tungsten alloy, plastic material loaded with radiopaque filler, and the like.

An important practical concern in thrombectomy procedures is the accuracy of the navigational process used to direct the endovascular placement of a thrombectomy device relative to the location of a thrombus. Magnetic resonance imaging can play an important role in localizing and characterizing the thrombus and in optimizing the positioning of the thrombectomy device. High-speed, high-resolution MR imaging can now be combined with conventional X-ray fluoroscopy and digital subtraction angiography (DSA) capability in a single hybrid imaging unit. New generations of MR scanners provide frequently updated images of the anatomical structures of interest. This real-time imaging capability makes it possible to use high-speed MR imaging to direct the movement of catheters and other components of the thrombectomy system to specific endovascular locations, and thereafter observe the effects of specific interventional procedures.

MR imaging is also valuable in assessing the presence and size of an intracranial thrombus and in characterizing its age and composition. A growing body of evidence suggests that a combination of MR imaging and neurologic symptoms may in fact have prognostic predictive value in assessing patient outcome. During formation of a thrombus, the blood contains a mixture of oxyhemoglobin, deoxyhemoglobin and methemoglobin that is usually equal to that of arterial blood. As the thrombus ages, however, the concentration of paramagnetic hemoglobin and methemoglobin within the clot also changes resulting in a characteristic appearance on MR images that reflects the age and stability of the clot. Observation of these MR imaging changes can be clinically useful in evaluating the potential utility of various alternative interventions, such as, for example, drug thrombolytic therapy versus mechanical thrombectomy.

The catheter tip on thrombectomy devices described in the prior art is difficult to see on MRI because of inadequate contrast with respect to surrounding tissues and structures. This makes accurate localization difficult and degrades the quality of the diagnostic information obtained from the image. Thus, one objective of this invention is to provide an MR-compatible and visible device that significantly improves the efficacy and safety of thrombus removal using MR guidance. For example, to enhance compatibility with MRI imaging systems, it may be desirable to make portions of the device in a manner that would impart a degree of MRI compatibility. For example, the device, or portions thereof, may be made of a material that does not substantially distort the image and create substantial artifacts (artifacts are gaps in the image). Certain ferromagnetic materials, for example, may not be suitable because they may create artifacts in an MRI image. The device, or portions thereof, may also be made from a material that the MRI machine can image. Some materials that exhibit these characteristics include, for example, tungsten, Elgiloy, MP35N, nitinol, and the like, and others.

Any material that might be added to the structure of a pliable catheter to make it MR visible must not contribute significantly to the overall magnetic susceptibility of the catheter, or imaging artifacts could be introduced during the MR process. It is also important that thrombectomy devices used under MR guidance are MR-compatible in both static and time-varying magnetic fields. Examples of such biocompatible and MR-compatible materials which could be used to practice the invention include elastomeric hydrogel, nylon, teflon, polyamide, polyethylene, polypropylene, polysulfone, ceramics, cermets steatite, carbon fiber composites, silicon nitride, and zirconia, plexiglass, and poly-ether-ether-ketone.

Although the mechanical effects of the magnetic field on ferromagnetic devices present the greatest danger to patients through possible unintended movement of the devices, tissue and device heating may also result from radio-frequency power deposition in electrically conductive material located within the imaging volume. Consequently, all cables, wires, and devices positioned within the MR imaging system must be made of materials that have properties that make them compatible with their use in human tissues during MR imaging procedures. Many materials with acceptable MR-compatibility, such as ceramics, composites and thermoplastic polymers, are electrical insulators and do not produce artifacts or safety hazards associated with applied electric fields. Some metallic materials, such as copper, brass, magnesium and aluminum are also generally MR-compatible, viz. large masses of these materials can be accommodated within the imaging region without significant image degradation.

Guidewires for the catheter component of the thrombectomy system are usually made of radiopaque material so that their precise location can be identified during a surgical procedure through fluoroscopic viewing. Exemplary of guidewires used under X-ray viewing is the guidewire disclosed by LeVeen, U.S. Pat. No. 4,448,195, in which a radiopaque wire can be identified on fluoroscopic images by metered bands placed at predetermined locations. U.S. Pat. No. 4,922,924, awarded to Gambale et al. discloses a bifilar arrangement whereby radiopaque and radiotransparent filaments are wrapped on a mandril to form a bifilar coil which provides radiopaque and radiotransparent areas on the guide wire. U.S. Pat. No. 5,375,596 to Twiss et al. discloses a method for locating catheters and other tubular medical devices using an integrated system of wire transmitters and receivers.

Initial attempts to position and visualize endovascular devices such as catheters in MR imaging were based on passive susceptibility artifacts produced by the device when exposed to the magnetic field. Magnetic susceptibility is a quantitative measure of a material's tendency to interact with and distort an applied magnetic field. U.S. Pat. No. 4,827,931, to Longmore and U.S. Pat. Nos. 5,154,179 and 4,989,608 to Ratner disclose the incorporation of paramagnetic material into endovascular devices to make the devices visible under MR imaging. U.S. Pat. No. 5,211,166 to Sepponen similarly discloses the use of surface impregnation of various "relaxants", including paramagnetic materials and nitrogen radicals, onto surgical instruments to enable their MR identification. An improved method for passive MR visualization of implantable medical devices has been disclosed by Werne in U.S. Pat. No. 5,744,958. In the method of the invention disclosed by Werne, an ultra thin coating of conductive material comprising 1-10% of the theoretical skin depth of the material being imaged is applied. By using a coating of 2,000-25,000 angstroms thickness, Werne has found that the susceptibility artifact due to the metal is negligible due to the low material mass. At the same time, the eddy currents are limited due to the ultra-thin conductor coating on the device.

However, these patents do not provide for artifact-free MR visibility in the presence of rapidly alternating magnetic fields, such as would be produced during echo-planar MR imaging pulse sequences used in real-time MR guided thrombectomy procedures. Nor do these patents teach a method for monitoring with MR-visible catheters the outcomes of therapeutic interventions, such as, for example, removal of a thrombus from the intracranial circulation followed by therapeutic drug delivery into brain tissues. Thus, there is a continuing need to develop an MR-compatible and visible thrombectomy device that does not obscure surrounding anatomy, and thereby compromise the physician's ability to perform the intervention.

The control wire(s) used to practice the present invention may be produced from any number of suitable materials having reasonable strength in tension, e.g., stainless steels, carbon fibers, engineering plastics, tungsten alloys, variously in the form of a multi-strand cable or single strand thread. Preferably, however, the wire may be made from a "so-called" super-elastic alloy. These alloys are characterized by an ability to transform from an austenitic crystal structure to a stress-induced martensitic (SIM) structure and to return elastically to the austenitic crystal structure (and the original shape) when the stress is removed. A typical alloy is nitinol, a nickel-titanium alloy, which is commercially available and undergoes the austenite-SIM-austenite transformation at a variety of temperature ranges. These materials are described, for instance in U.S. Pat. Nos. 3,174,851 and 3,351,463. These alloys are especially suitable because of their capacity to elastically recover almost completely to the initial configuration once the stress is removed. Since this is so, the size of the actual wire may be made fairly small, e.g., as small as 0.005 inches in diameter or smaller, and the resulting device is able to access very small regions of the body. The wire may also vary in diameter along its length, for example have a larger diameter at the proximal end as compared to the distal end or vice versa.

The wires can have a proximal section and a distal section. The proximal section preferably has a uniform diameter of at least about 0.0001 inch, or about 0.005 to 0.025 inches, preferably 0.0010 to 0.018 inches. Commercially available wires with a material (wire) diameter of 0.008 mm and a loop diameter of 1 mm are available as microcoil materials. Optionally, the distal section that may extend beyond the catheter may have different (more or less) flexibility than the proximal section. Typically, both sections will extend from the distal and proximal ends of the catheter lumen. The wire may have a middle section having a diameter intermediate between the diameter of the two portions of the wire adjoining the middle section or the middle section may be continuously tapered, may have a number of tapered sections or sections of differing diameters, or may be of a uniform diameter along its length and be tapered at or near the distal section. The entire wire may be between about 50 and 300 cm, typically between about 175 to 190 cm in length. The wire may be wrapped to form a coil section or may be independently attached to a coil.

The overall length of the pusher wire, pull wire, and soft coil mesh may extend through a catheter and the wires and catheter inserted into the vasculature. The catheter and wires (with attached soft coil) may extend proximal or distal to the site of the clot or the catheter may be positioned and the wires extend to the site from the catheter. The configurable soft coil component of the device is positioned near the target thrombus site, and the wires position and control the positioning and attitude of the soft coil capture components.

FIG. 5A shows the capture device in a format of providing two distinct macrocoil/microcoil systems 132 and 134, with individual insertion elements 142 and 144. Both macrocoil/microcoil systems 132 and 134 are shown separately deployed and not yet engaged with each other. In a preferred embodiment, each macrocoil/microcoil systems 132 and 134 would also have a pull string or retraction wire (not shown) on the ends of the macrocoil/microcoil systems 132 and 134 most distal from the thrombus 72.

Figure 5B:
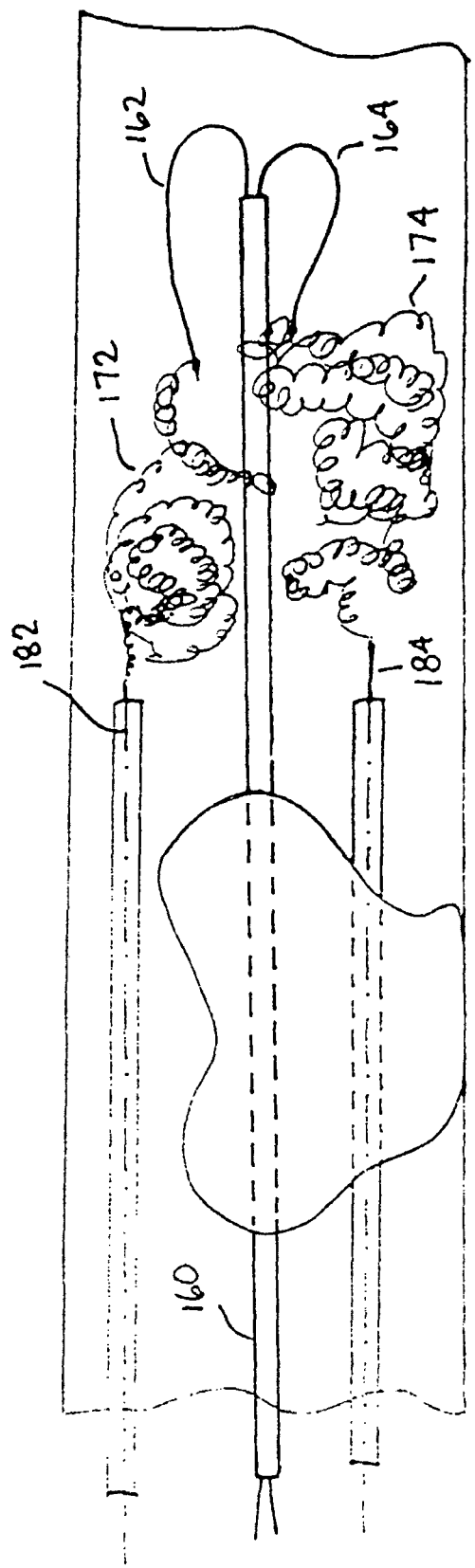
FIG. 5B shows the capture device in a format of providing two distinct macrocoil/microcoil systems with separate extraction strings or separate retraction strings.

FIG. 5B shows the capture device in a format of providing two distinct macrocoil/microcoil systems 172 and 174 with separate extraction strings 162 and 164 provided through a third catheter 160 or separate retraction strings or pull strings 182 and 184, respectively.

Figure 6:
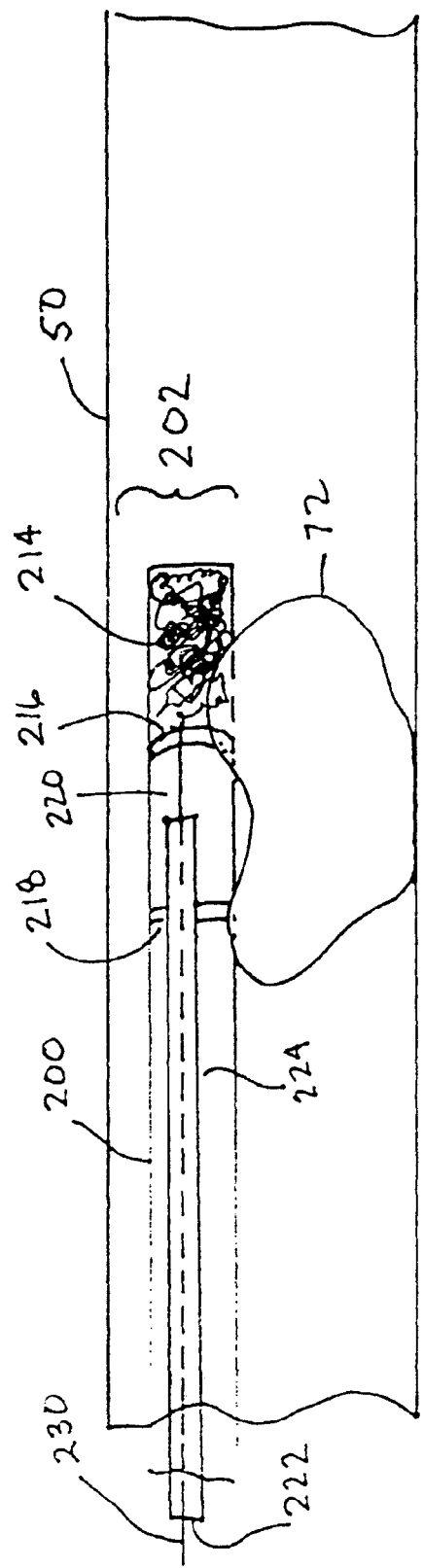
FIG. 6 shows a pneumatic delivery microcatheter delivery system with constrained coils within the catheter.

FIG. 6 shows a pneumatic delivery microcatheter delivery system with constrained coils within the catheter. FIG. 6 shows delivery system 202 comprising a catheter 200 having the confined mass of the macrocoil/microcoil material 214 before deployment of the microcoils within the lumen of the catheter. Within the catheter 200 are two sealing elements 218 and 216 that form a pressurable zone 220 within the catheter 200. The forward seal 216 is capable of being moved forward within the catheter 200 by increased pressure within the zone 220. A microcatheter 224 is within the catheter 200 and a lumen 222 within the microcatheter 224 carries fluid pressure and the retraction wire 230 into the pressurable zone 220. When pressure in the zone 222 is sufficient, the forward seal element 216 will press the compressed macrocoil/microcoil mass 214 out of the catheter 200. The seal 216 will be restrained by the retraction wire 230 that also is secured to one end of the contained mesh material 214.

Figure 7:
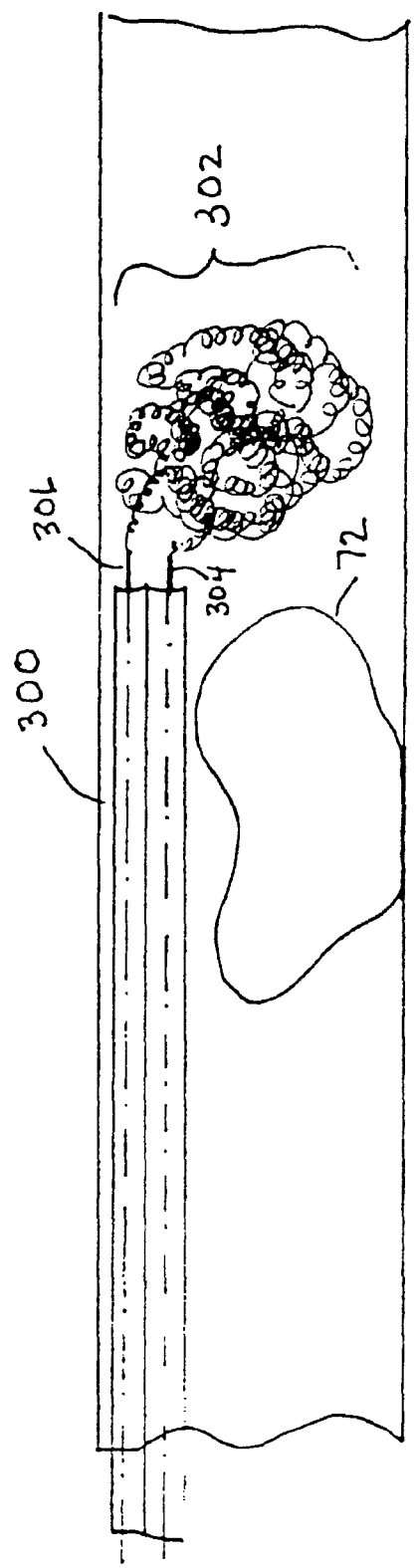
FIG. 7 shows a dual lumen catheter system deploying two macrocoil mesh elements, each with separate end controls of a mesh wire, which have entwined beyond a thrombus.
Figure 7A:
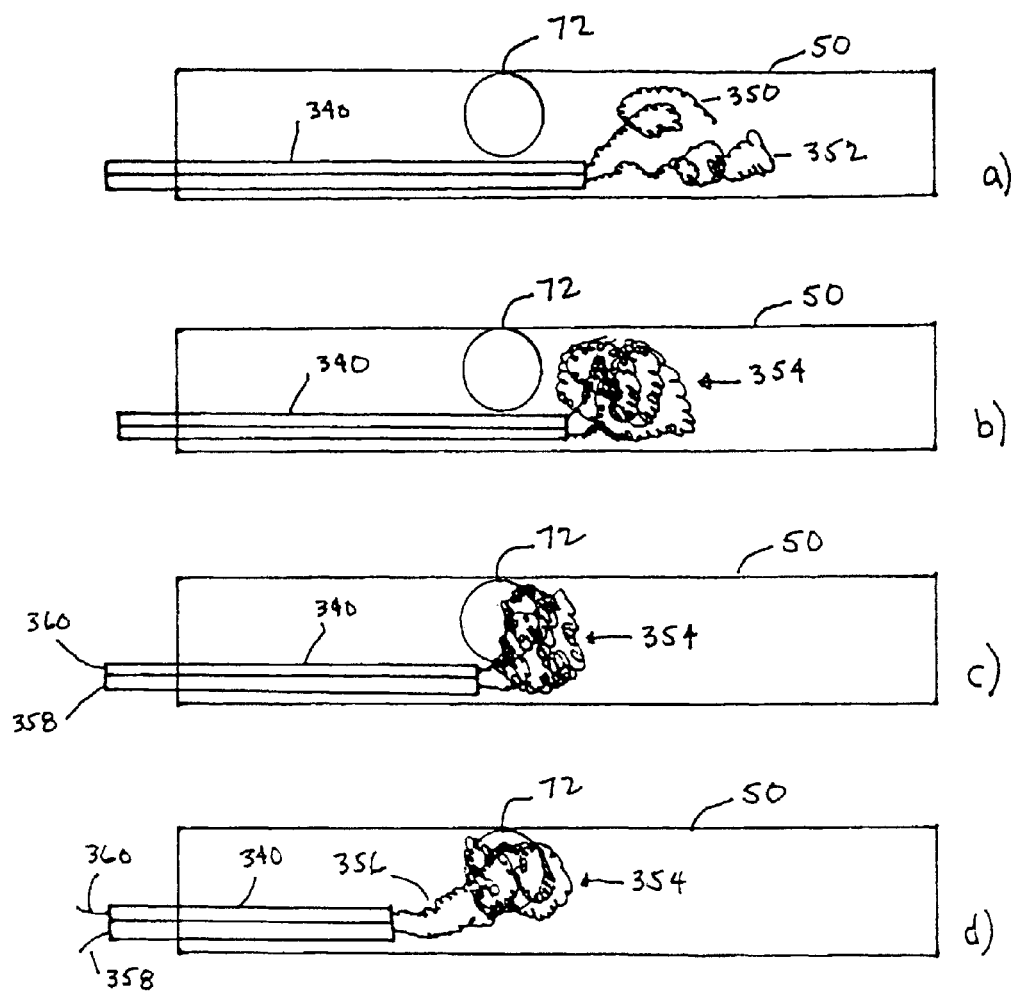
FIG. 7A shows a series of steps in which a dual lumen catheter is deploying two macrocoil mesh assemblies, each with separate end controls of the mesh wire in each lumen. The macrocoils have entwined and progressively encircle the thrombus as the microcatheter is withdrawn.

FIG. 7A shows a two-lumen microcatheter 300 providing the macrocoil/microcoil mesh 302 with two separate control wires 304 and 306 acting as the insertion wires. Retraction or pull wires are not shown but are similar to those in FIGS. 1-3. The macrocoil/microcoil mesh 302 is shown deployed beyond the thrombus 72.

FIG. 7B shows a series of steps a) b) c) and d) in which a dual lumen catheter 340 is deploying two microcoil/macrocoil mesh assemblies 350 and 352 to form an engaged single macrocoil mesh 354 with separate end control of the mesh wire in each lumen. The last three steps b) c) and d) represent a single mesh 354 delivered from the two adjacent lumens in a microcatheter 340, progressively encircling the thrombus 72. Two separate control ends 358 and 360 for controlling the composite mesh 354 are shown.

Figure 8:
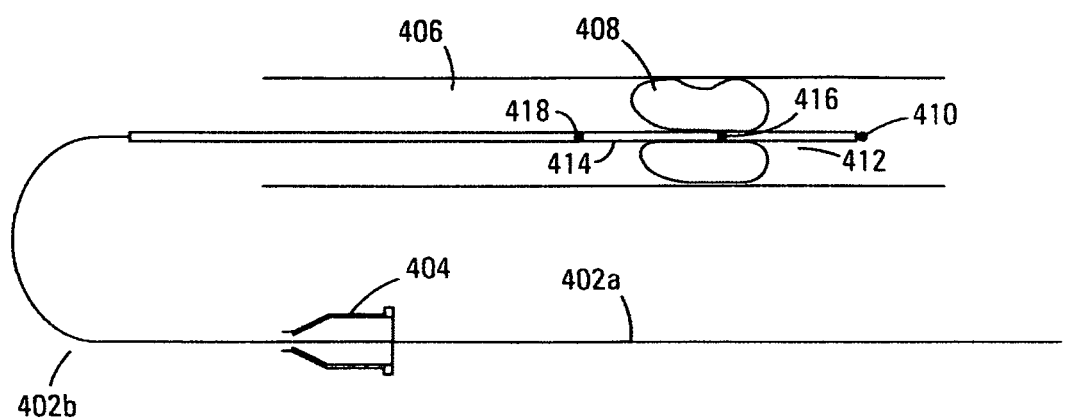
FIG. 8 shows placement of a distal tip with multiple release segments beyond a clot.

FIG. 8 shows placement of a single microcatheter carrier with a dual displacement coil system 402a having a distal tip 410 with multiple release segments 412 and 414 beyond a clot 408. Using a standard guidewire 402b, a catheter is inserted into a vessel 406 (e.g., vein, artery, duct, tube or other biological vessel). The inserted portion of the device 402b is shown with a distal displaceable coil segment 416 and a proximal displaceable coil segment 414 distributed between the distal tip 410, a spacing element 416 and a blocking element 418 that defines the relative release positions of the two displaceable coil elements 412 and 414. The inserted section of the device 402b is shown with the spacing element 416 within the zone defined by the clot 408.

Figure 9A:
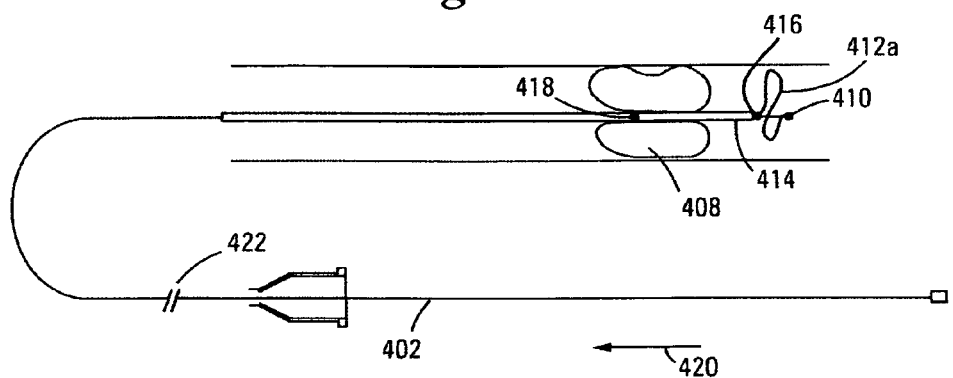
FIG. 9A shows the advance of a cannula/coil to form a complex coil shape distal to the clot.

FIG. 9A shows the advance of a cannula/coil blocking element 418 towards and into the clot 408 to form a complex coil shape 412a distal to the clot 408. The movement of the spacing element 416 forward and/or movement of the tip 410 rear-ward (with forward along the length of the device 402 denoted by arrow 420 causes displacement and/or deployment of the distal segment (412 in FIG. 8) macrocoil to form a complex shape 412a. With the Core Wire held stationary, the practitioner advances the Hollow Cannula/Shape Coil Assembly. The assembly continues to be advanced until the Distal Eyelet Coil is near the Tip Coil as shown in FIG. 9A.

Figure 9B:
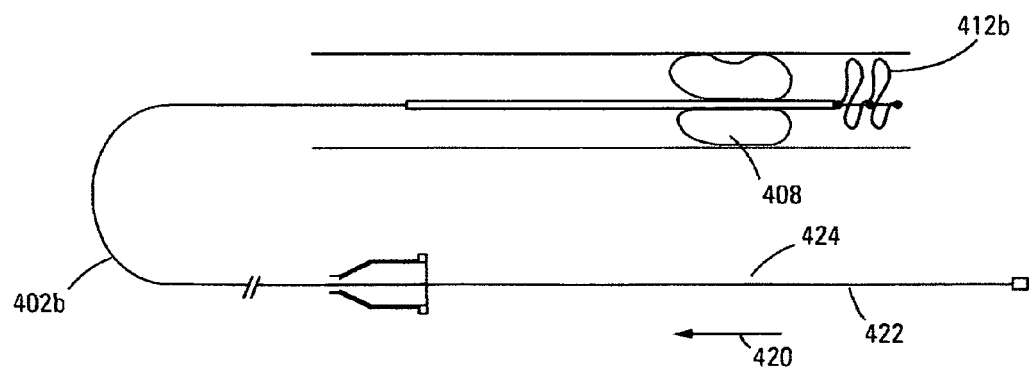
FIG. 9B shows the further advance of a cannula/coil to form a more complex coil shape distal to the clot following the initial displacement of FIG. 9A.

FIG. 9B shows the further advance along direction 420 of a cannula/coil 402b to form a more complex coil shape 412b distal to the clot 408 following the initial displacement of FIG. 9A, while the core wire 422 is maintained in a stationary position as a sheath 424 is advanced to further deploy and compress the coil segment 412b. This process continues by advancing the Hollow Cannula/Shape Coil Assembly until the Proximal Eyelet Coil is near the Distal Eyelet Coil as shown in FIG. 9B. At this position, the Shape Coil has formed a complex geometric shape capable of conforming to and retaining the clot.

FIG. 9C shows the displacement of a cannula/coil sheath 424 to form a second displaced coil element segment 414a on the proximal side of the thrombus 408 after the formation of the more complex coil shape 412b in FIG. 9B. It can be seen that the same coil strand or two distinct coil strands can be used to form the confining loops 412b and 414a that surround and support the clot 408. Depending upon events and controls exercised in the deployment of the coil segments 412b and 414a, part of one or both strands may also form body entrapment 428 of the clot 408.

FIG. 9D shows the retraction of the device 402a after the cannula/coil on the proximal side 414a of the thrombus 408 has been achieved, thus removing the clot 408 while supported on both the distal 412b and proximal 414a sides of the thrombus 408. It should be mentioned that even though these figures show the device passing through a center opening 430 of the clot 408, many clots form on a single side of a vessel or do not form on all sides of a vessel to form a tunnel, and the device may pass around the clot and not necessarily through the clot.

FIG. 10A shows a complete assembly 500 separately magnified for better definition. The assembly has an insertion tip 510 distal shape coil segment 512, proximal shape coil segment 514, a hollow cannula 532, transition coil 540, core wire 542 and end cap 544. Also shown are the distal eyelet coil 516 functioning as a separator between the distal shape coil segment 512 and proximal shape coil segment 514, and a proximal eyelet coil 518 stabilizing the proximal shape coil segment 514. In the expanded segments in FIG. 10A, larger views of the core wire 542, distal eyelet coil 516, tip coil 510, weld 546, proximal eyelet coil 518 and other elements are shown. In the other expanded segment of FIG. 10A, the core wire 542, the distal shape coil 512 and the hollow cannula 532 are shown. In one non-limiting description of the structure of the device, the device is similar in general design to a vascular guidewire. In FIG. 10A is a sketch of the Device design having a Shape Coil element attached to a Hollow Cannula via a short Transition Coil. Within the Hollow Cannula is a Core Wire that is attached to the distal tip of the Proximal Coil. The Core Wire exits the Hollow Coil through the Transition Coil and runs alongside the Shape Coil until it terminates at the Device tip. At two locations along the Shape Coil, the Core Wire is threaded through Eyelet Coils that may be coaxially welded to the Shape Coil. At the distal end of the Device, the Core Wire may be welded to the Shape Coil through the use of a short Tip Coil. The proximal end of the Core Wire extends beyond the proximal end of the Hollow Cannula and is terminated with an End Cap. The Shape Coil/Hollow Cannula assembly is slideable relative to Core Wire. The major outside diameter of the device is 0.016" and is designed to be inserted through a micro-catheter with an internal lumen of 0.018". The entire length of the device is 200 cm.

There are a range of variations for the dimensions of the device, a very narrow range of non-limiting examples is described below, with ±20 variation expected in particular designs and uses in other locations.

TABLE 1

Design Variants

| Variant | Range |
|---|---|
| Major Diameter | 0.014" to 0.018" 0.010" to 0.024" |
| Overall Length | 150 cm to 300 cm 100 cm to 500 cm |
| Shape Coil Length | 5 cm to 30 cm 3 cm to 50 cm |
| Number of Eyelets | 1, 2, 3, 4, or 5 or more |
| Materials | |
| Hollow Cannula | Stainless Steel or Nitinol |
| Shape Coil | Stainless Steel, Platinum, or Nitinol |
| Transition Coil | Stainless Steel, Platinum, or Nitinol |
| Eyelet Coil (2) | Stainless Steel, Platinum, or Nitinol |
| Tip Coil | Stainless Steel, Platinum, or Nitinol |
| Core Wire | Stainless Steel, Polyethylene, Nylon, or Nitinol |

Another range of dimensions that should be considered as a narrow range of preferences that should not limit the scope of the invention are shown in Table 2.

TABLE 2

Component Description

| Component | Dimensions | Material |
|---|---|---|
| Hollow Cannula | 0.006" ID × 0.012" OD | Stainless Steel |
| Shape Coil | 0.005: ID × 0.010" OD | Stainless Steel |
| Transition Coil | 0.013" ID × 0.016" OD | Stainless Steel |
| Eyelet Coils (2) | 0.013" ID × 0.016" OD | Stainless Steel |
| Tip Coil | 0.013" ID × 0.016" OD | Stainless Steel |
| Core Wire | 0.003" OD | Stainless Steel |

The coil product may be provided in packaging as a loop of the coil in wrapping, such as bubble wrap, packets, paperboard supporting a cover, and any other format of packaging that protects the device and preferably keeps the device in antiseptic conditions. For example, the Device is intended for one time, sterile use. It could be inserted into a rigid polyethylene tube Carrier. The Carrier will be inserted into a Tyvek/polyethylene pouch pre-sealed on three sides. The pouch will then be heat-sealed closed and a label placed on the clear polyethylene film. The sealed pouch along with an Instruction for Use will be inserted into an appropriately sized carton. The carton label, similar to the pouch label, will be applied over the edge of the carton to allow label information to be displayed on the front, side, and back panels.

FIG. 10B shows a cross-section 600 of a portion of the device of FIG. 10A near an eyelet (not shown). The cross-section 600 shows the exterior eyelet coil 602 the structurally supporting shape coil 612, the guiding and structurally supporting core wire 642 and a weld joint 660 between the shape coil 612 and the eyelet coil 642.

Alternative processes and constructions could provide a soft coil capture device (macrocoil/microcoil mesh) which may be of larger or smaller dimensions than typical intravascular devices. With small coils, but particularly with larger coils, greater strength may be built into the elastic memory of the material, and the length of the remembered coil distribution within the macrocoil element may be increased or decreased. The coil material may be delivered through a catheter or microcatheter, with the elongation of the coils controlled by relative positioning of the push (insertion) and pull (retraction) wires as explained above. One end of the coil material may be secured to the push (insertion) wire, and the distal (leading end) of the coil material may be secured to the distal end of the pull (retraction) wire. When in a fully deployed state, without tension applied by the wires, a natural distribution (frequency) of the macrocoils may exist, but this is not a true memory shape. It is only the random structure of the macrocoils and microcoils. Points of contact between the macrocoils and the pull wire are preferably not secured, rather, the macrocoils are able to slide freely. If the contact points were secured, the frequency between the coils would not be fixed after deployment, since the pull wire is able to telescope or otherwise extend the distribution of the macrocoils within the mesh. The macrocoils, when in a region for deployment, without a restraining action through the connection at the distal connecting point, may have a greater frequency (less spacing) between the macrocoils. The microcoils and macrocoils may be manufactured and designed so as to provide natural dimensions when tension is released after deployment to fit a range of dimensions in the vasculature. The selection of the microcoil size, microcoil spacing, wire thickness, wire material, macrocoil size, and macrocoil spacing are used to determine the frequency, size and shape of the deployed structure.

One major embodiment of this technology is for a Mechanical Retrieval Device (Device) that is a single use medical device. The Device is intended to be used to safely and effectively remove obstructions from blood vessels in the human body.

One embodiment of the Device comprises thin wire coils placed within a microcatheter having a small internal diameter (0.024" or less). A guide catheter of larger diameter is positioned using angiography guidance into the blood vessel that contains the obstruction. The microcatheter may be inserted through the guide catheter and led by a microguidewire to pass between the obstruction and the lumen wall. The microguidewire is retracted and soft platinum coils are passed through the microcatheter on the distal side of the obstruction. The microguidewire is then retracted further to permit platinum coils to be placed on the proximal side of the obstruction. Portions of the coils then wrap around the obstruction, producing a mesh that prevents fragmentation of the obstruction. The mesh and knot are tightened mechanically using a pull string and the mesh and obstruction are pulled back toward the end hole of the guide catheter. Whenever possible, the obstruction is pulled into the guide catheter and out of the body. If the obstruction is too large to be removed through the guide catheter, the guide catheter and obstruction are withdrawn together.

Among the benefits of this type of system is that the Device design is intended to allow easier access into anatomically difficult locations because it is pushed out of a microcatheter. Other devices such as those delivering laser, ultrasound, or photo-acoustical energy may be too stiff to access tortuous blood vessels, and too large to pass through a small microcatheter. The Device can remove both soft and hard obstructions including blood clots and catheter fragments and coils. Other types of devices that are small enough to pass through a microcatheter are typically indicated for removal of soft materials such as an acute thrombus, and might be able to snare a foreign body. By comparison, our Device can fully enmesh and remove a hard object, such as a fibrin-laden thrombus. The Device can also remove soft materials, such as acute thrombus which becomes adherent to the coils of the Device. The Device is also designed to enmesh and retrieve a coil or catheter fragment dislodged during an intravascular procedure. The Device features a series of soft platinum coils that may come into contact with the walls of blood vessels. Our preclinical studies indicate that these coils will not damage blood vessel walls, a crucial feature when working in arteries in the head and heart.

The Device is similar in general design to a vascular guidewire. A sketch of the Device design is shown below in FIG. 11. The Device in FIG. 11 consists of a platinum coil element 802 attached to a stainless steel hypo tube 804 via a polyimide transition tube. Within the tubes and coil element is a stainless steel core wire 808. A protective shrink tube 810 covers the transition tube 806 and the distal end 812 of the hypo tube 804 to create a smoother, more lubricious surface. Eyelets 814 in the coil elements 802, the distal tip 816 of the coil elements 814 and the core wire 820 are also shown in FIG. 11.

In the midsection of FIG. 11 is shown an expanded view of the coil elements 802 with the eyelets 814, distal tip 816 and core wire 820 shown. In the two FIG. 11 segments at the bottom, further views can be seen, wherein a single coil element 802 (which might be delivered through a single lumen catheter, not shown) has formed loops 826 because the core wire (not shown) has been retracted, putting tension on the coil elements, to form the loops 826. A further view at the bottom of FIG. 11 shows the physical relationship between an unretracted coil element 802, an eyelet 814 and the core wire 820. As can be envisioned, when the core wire is retracted, tension is passed down through the coil elements, and the tension is relieved in part by forming the loops 826. The structure of the loops can be somewhat controlled by spacing of the eyelets (which will assist in the definition of the size of loops) and other structural variations.

Near the distal tip of the device, the core wire exits the Device and runs alongside the coil element, re-entering the coil element at defined eyelets. The eyelet portion of the coil element forms discrete loops when the user retracts the proximal end of the core wire. Proximal to the eyelet section, the coil element may be pre-shaped to form a spiraled coil shape. These coils, along with the user activated distal loops, are used to capture and retrieve a blood clot or other obstruction.

One example of a major outside diameter of the device is 0.021" at the eyelet locations and is designed so that it can be inserted through a microcatheter with an internal lumen of 0.024". The entire length of the device may be 175 cm.

A general principle of operation for systems according to the present technology is shown in FIG. 12. The principle of operation is illustrated in FIG. 2. The Device is inserted into a microcatheter that is already placed distal of the obstruction. The Device is advanced and then actuated to form the distal Loops. These Loops act as a cap. Alone, the Loops may or may not grab the obstruction. To ensure retrieval, the pre-shaped coils are advanced out of the microcatheter. These coils are placed both distal and proximal of the obstruction. Once placed, the core wire is further retracted to tighten the coil structure around the obstruction. The obstruction, now fully sandwiched or cocooned within the coil element, can be safely removed.

The device and technology of FIGS. 11 and 12 may be further described as follows. A medical device is provided for removing a solid object such as a thrombus from vessels, such as a blood vessel. One format of the device shown and already described for FIG. 11 has at least one microcatheter lumen, the at least one microcatheter lumen having at least one deployable macrocoil having a length. A single microcatheter lumen may carry one or more of the macrocoils, or multiple microcatheter lumens may each carry one or more macrocoil elements. The preferred macrocoil element is flexible and conformable. The most preferred macrocoil element comprises a continuous region of microcoils (that is substantially the entire length of the macrocoil comprises the microcoils described herein, with few or no interruptions between the microcoils, except as explained herein possibly eyelets formed from the microcoils being dislocated from the macrocoil, as by punching, pressing, twisting or other physical dislocation) or at least two separate macrocoils segments comprising regions of microcoils therein (e.g., the length of the macrocoil may be interrupted by short straight sections, stiffened areas, flexibilized areas, etc.). Each of the at least one macrocoils should be capable of separate deployment from the microcatheter lumen. Each of the macrocoils should be capable of conforming to a solid object of a size range of solid objects expected within the vessel. The microcoil regions or segments of the macrocoil should be flexible along a length of the deployable macrocoil, and each of the at least one deployable macrocoil, when deployed to a location outside of the microcatheter, are capable of being withdrawn from the location by withdrawal of the lumen. At least one of the at least two macrocoil segments should act as a macrocoil engaging component for a solid object e.g., thrombus or deposit). The macrocoil thrombus engaging component has a length with a proximal end and a distal end, the length of the macrocoil thrombus engaging component comprised of microcoils that allow the length of the macrocoil segment to be extendable and flexible. The device may also feature at least two macrocoil segments where each comprises a macrocoil thrombus engaging component having a length with a proximal end and a distal end, the length of each of the at least two macrocoil segments comprised of microcoils that allow the length of each macrocoil segment to be independently extendable, conformable and flexible.

An alternative description of elements for the practice of the present technology is as a medical device for removing a thrombus from a blood vessel comprising at least one microcatheter lumen having a length between a distal end and a proximal end, the at least one microcatheter lumen having within the at least one microcatheter lumen at least one region of a positionable and deployable macrocoil. The deployable macrocoil is deployable from the distal end of the microcatheter lumen and positionable about a shaped structure within a blood vessel distally located with respect to the length of the lumen. This device should have the macrocoil is conformable about the shaped structure because of flexibility and conformability in the macrocoil provided by microcoils within the macrocoil. The shaped structure usually comprises a thrombus within the blood vessel. The conformability is necessary because there is no uniform or unique shape for all thrombi. A method of capturing a solid object within a vessel in a patient would include inserting a medical device for removing a solid object from a vessel, the device comprising the device described directly above. The method would insert the medical device into a blood vessel so that a the microcatheter lumen is not beyond the solid object, deploy a first at least one deployable macrocoil beyond the solid object to provide a distal engaging element beyond the solid object and deploy a capture element for the shaped structure that is not beyond the solid object to form a proximal engaging structure for the solid object comprising the distal macrocoil and the capture element on relatively opposite sides of the solid object. This is clearly illustrated in FIG. 12, using a general device such as the specific device shown in FIG. 11. The method could continue by after forming the distal engaging structure and the proximal engaging structure, directing the at least one deployable microcoil to conform to the solid object, and then withdraw the medical device to withdraw the solid object from the vessel or move the solid object within the vessel.

Another description of a method of capturing a solid object within a vessel in a patient comprising inserting the medical device described above would include: inserting the microcatheter lumen into a patient so that a first at least one deployable microcoil region or segment is beyond the solid object and a second at least one other microcoil region or segment is not beyond the solid object, using the first at least one deployable macrocoil beyond the solid object to provide a distal engaging element of a microcoil segment beyond the solid object and deploying the second at least one other microcoil segment not beyond the solid object to form a proximal engaging structure for the solid object. This method may include steps after forming the distal engaging structure and the proximal engaging structure, including withdrawing the medical device to withdraw the solid object from the vessel or move the solid object within the vessel.

An alternatively described device for retrieval of objects from within vessels of patients would include: a length of microcoil having approximately helical turns continuously or within adjacent sections of the length of microcoil and the helical turns have an average diameter, at least some of the continuous length or the segments in the length of microcoil having eyelets that extend beyond the average diameter, and a core wire passing through at least some adjacent eyelets from a distal end to a proximal end of the length of microcoil, the core wire being restrained near the distal end of the length of microcoil. This device would prefer having the average diameter of the helical turns as less than 0.050 inches. The device would be carried within a lumen of a microcatheter wherein the lumen internal diameter is greater than the average diameter of the helical turns of the length of microcoil. The device would operate by tension applied on the proximal end of the core wire causing the length of microcoil to form loops outside of the average diameter of the length of microcoil. As is shown in FIG. 11, the loops are shown relatively uniform in size, but this is not required. The size of the loops is controlled and affected by the amount of tension, the spacing of the eyelets, size of segments and other controllable structural features. The loops need not be so circular in shape, and in fact, because of the use of random microcoil structures that have no absolute and elastic memory shape, the coils can conform to the surface of the solid object and tend to not be uniform in at least shape and often in size during use. Also as shown in FIG. 12, the more distal region of the macrocoil forms a more random and bunched up shape in conforming the distal side of the thrombus, while the more proximal region of the macrocoil tends to remain more liner, more helical, or more uniform in shape as it tends to lightly receive or support the thrombus and does not have to conform intimately with the surface of the thrombus.

Another alternative description for a device for insertion into a vessel from the removal of at least one solid object from within the vessel can be provided as comprising: a catheter having a lumen; within the lumen of the catheter is at least: one macrocoil elongate element having an axis and a length, multiple eyelets on the macrocoil elongate element that extend away from the axis, and a core wire extending through at least two of the multiple eyelets; wherein the core wire is attached at a distal point along the length of the macrocoil, wherein increasing tension on the core wire, which tension is in part guided by the core wire passing through multiple eyelets, causes the macrocoil to form loops, curves, bundles or a non-linear compressed shape. This device may have the macrocoil element consist of or comprise a continuous length of microcoils or segments of microcoils along the length of the macrocoil that add flexibility and conformability to the macrocoil. The macrocoil element may preferably comprise a continuous length of microcoils, which may be interrupted by eyelets formed from the microcoils. Eyelets may be formed along the length of the macrocoil element by dislocated microcoils extending away from the axis of the macrocoil elongate element and providing openings through which the core wire may pass. When tension is applied to the core wire, the macrocoil forms loops along the length of the macrocoil. The tension on the macrocoil is imposed on the distal end at the point of connection and pressure applied at the eyelets. Because of pressure at the eyelets, at least some loops likely will be formed adjacent at least one eyelet, sometimes with at least one eyelet approximately defining a beginning of a loop.

A method of removing a solid object from a vessel using the immediately described device could include steps such as: inserting the catheter into a vessel adjacent a solid object in the vessel; extending at least a distal end of at least one macrocoil element beyond the solid object, away from the catheter; applying tension to the core wire; retracting the at least distal end of the macrocoil element to reshape the at least one macrocoil and conform at least a portion of the macrocoil to a surface of the solid object; and withdrawing the macrocoil element and moving the solid object.

Figure 13:
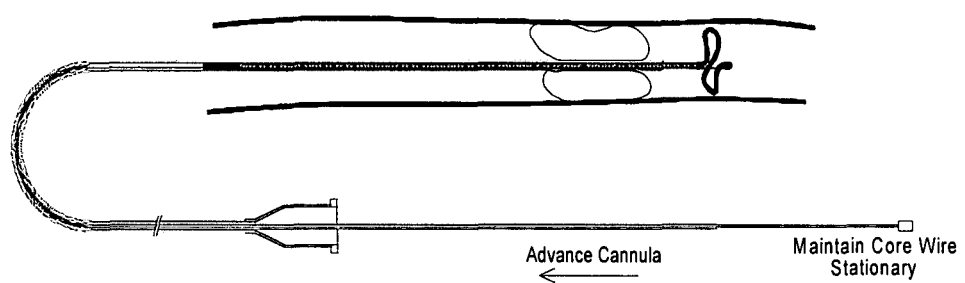
FIG. 13 further shows the operation of the mechanical thrombectomy device according to the present invention.

FIG. 13 further shows operation of a mechanical treatment device as The Device comprises thin wire coils placed within a microcatheter having a small internal diameter (0.024" or less). A guiding catheter of larger diameter is positioned using angiography guidance into the blood vessel that contains the obstruction. The microcatheter is inserted through the guiding catheter and led by a microguidewire to pass between the obstruction and the lumen wall. The microguidewire is removed, and the coils are passed through the microcatheter. Portions of the coils then wrap around the obstruction producing a mesh that prevents fragmentation of the obstruction. The mesh and knot are tightened mechanically and the mesh and obstruction are pulled back into the end hole of the guiding catheter. Whenever possible, the obstruction is pulled into the guiding catheter and out of the body. If the obstruction is too large to be removed through the guiding catheter, the guiding catheter and obstruction are removed together. This device may be described as a device for retrieval of objects from within vessels of patients comprising a length of microcoil having approximately helical turns within section of the length of microcoil and an average diameter of the helical turns, at least some of the segments in the length of microcoil having eyelets that extend beyond the average diameter, and a core wire passing through adjacent eyelets from a distal end to a proximal end of the length of microcoil, the core wire being restrained near the distal end of the length of microcoil. The average diameter is preferably less than 0.050 inches. The device may be carried within a lumen of a microcatheter wherein the lumen internal diameter is greater than the average diameter of the length of microcoil. The tension applied on the proximal end of the core wire will cause the length of microcoil to form loops outside of the average diameter of the length of microcoil.

Although the examples show specific dimensions and materials, the examples and descriptions are not intended to be limiting to the scope of practice and protection of the technology described. Rather, any specific statements or values are intended to be examples within the generic concepts of the inventions and the disclosure taught and provided herein.

Experimentation with the Thrombus Removal System has been conducted in order to remove both soft and very firm clot from the arterial lumens of multiple arteries (renal, subclavian, common and internal carotid arteries) in the pig model. Soft clot was only a few hours old. Hard clot was made by allowing a pig's blood to stand for four days. The firm, fibrin-containing portion separated from the plasma, and the hard clot embolized into the selected artery of a second pig.

Both complex three-dimensional and less complex two-dimensional platinum coils were used in these experiments, including coil structures that were not designed for use in thrombectomy procedures, but rather being the commercially available types used to fill cerebral aneurysms. These coils have a variable cross-sectional diameter and length, and are attached to a stainless steel pusher wire. A commercially available microcatheter with an inner lumen of 0.018 inch was passed beyond the thrombus, particularly between the intima and the thrombus (non-occluded space between the thrombus and the walls) in the case of a firm thrombus, with the aid of a commercially available 0.014 inch microguidewire. A thin nylon line (0.006 inch) was attached to the distal end of a coil, and the coil/string complex gently passed into a microcatheter, to a point distal to the thrombus. Alternatively, the coil/string complex was preloaded into the microcatheter that was passed without the aid of a microguidewire past the distal end of the thrombus. The coils were pushed from the microcatheter, which was progressively pulled back until it was proximal to the thrombus and clot extraction attempted, as previously described.

Soft clot tended to be removed easily from the arteries studied because the clot adhered to the meshwork of the coil and the pulling wire. However, initial experiments with single coils of different sizes, including both 3-D and 2-D coils, demonstrated the inability to consistently and successfully extract the firm clot with this method, even when the coil had formed a mesh around the thrombus and the nylon string was pulled as much as possible to tighten the mesh around the clot. Rather, the coil sometimes simply unraveled from around the thrombus, sliding back into the more proximal microcatheter. It was apparent that in those failed circumstances the loops of the coil were simply wrapping around the clot without becoming tightly engaged, and that such a non-structured mesh was insufficient to overcome the combination of forces keeping the thrombus in place, including friction between the thrombus and the intima and blood flow pushing the embolus distally. However, intertwining and/or overlapping of the loops along the distal aspect of the thrombus, as one would tie a shoelace, kept the distal mesh in place without allowing the entire coil complex to unravel.

In subsequent experiments, two microcatheters were passed distal to the firm clot, each positioned in the same manner as previously described. The distal end of a 3-D coil was pushed into the arterial lumen from the first microcatheter, then the distal end of a second coil, either a 2-D or a 3-D configuration, was pushed forward from the second microcatheter, allowing loops of the two coils to intertwine. By "two coils" in this description, it is meant that there are two masses of coils, one each delivered from a microcatheter, although the term includes two coil masses emanating from two lumens of a single microcatheter, as opposed to requiring two completely distinct microcatheters. Further coils were extended to make a complex, random mesh, then the nylon strings were pulled so that a tight "cap" or "knot" was formed on the distal surface of the clot. The microcatheters were partially withdrawn and as more coils were pushed from the microcatheter, they passively encircled the middle portions of the clot. The process was continued, with more coils (at least a total of two and up to six coils would be used in a preferred range of mesh applications) placed proximal to the clot. The nylon strings was then pulled tightly to form a tight meshwork encircling the entire clot so that little or no fragmentation would occur.

Using this technique, it was possible to successfully extract firm clots from all arteries embolized without evidence of fragmentation on subsequent post-extraction angiography. Coils having diameters equal to or slightly larger than that of the arterial lumen appeared to make the best distal meshwork and, therefore, the most stable macrocoil constructs. By then passively encircling the clot, there was no tendency for the distal "cap" to simply slide from the top over the side of the clot. Post-extraction angiography and post-mortem examination, including microscopy, did not demonstrate any evidence of arterial injury. This was the expected result, given the extensive experience of using these soft platinum coils within the vascular system without producing vascular dissection or vasospasm.

Another way of generally describing articles and methods according to the practice of the technology originally disclosed herein includes a medical device for removing a thrombus from a blood vessel, comprising: a) two microcatheter lumens, each lumen containing: b) a macrocoil thrombus engaging component having a length with a proximal end and a distal end, the length of the macrocoil comprising microcoils that allow the length of the macrocoil to be extendable; c) a first wire capable of providing force on the distal end of the macrocoil; d) a second wire capable of providing force on the proximal end of the macrocoil. The device may have at least two lumens on distinct microcatheters, and the at least two lumens may be attached to a single catheter. A method may be practiced for using the device wherein for at least one macrocoil thrombus engaging coil, a microguidewire is passed through at least one of the lumens to help place the microcatheter distal to the thrombus; the microguidewire is removed; a macrocoil pull-string system comprising push-pull capability is passed through the at least one of the lumens; the macrocoil pull-string system is passed distal to the clot; the pull-string system is used to form an at least partially enclosing distal meshwork on the distal surface of the thrombus, passively encircling mesh around the clot; the pull string is pulled to tighten the meshwork; the macrocoils may have internal structures including loops and other random attachments to facilitate the formation of a tight meshwork; and at least a portion of the device is progressively withdrawn so that the meshwork becomes more tightly engaged with the clot. The method of using the device may be practiced wherein the at least one set of microcoils of at least one macrocoil exhibits a conformation memory of an amorphous shape with overlapping structure resisting complete elongation when ends of the at least one macrocoil are stressed. The conformation memory may form at least one structure selected from the group consisting of knots, loops, multiple crossovers, kinks and snags to reduce excessive slipping of macrocoils, which slipping would allow liner extension of macrocoil material. The method may have the at least one structure assist in forming a network comprising the at least one macrocoil engaging a distal surface of the thrombus. The method may be practiced so that the at least one macrocoil encircles or conforms to the surface of the distal side of the thrombus as the at least one macrocoil is extended from the microcatheter. The method may use a pull-string to tighten the at least one macrocoil against the distal side of the thrombus.

A dual lumen catheter or two separate catheters may deploy a single macrocoil mesh with controls on both ends, or two separate meshes, each with one or two separate end controls of the macrocoil mesh in each lumen. Examples of the end control elements are a pull wire or push pull wire attached to either end of the macrocoil mesh. A thrombus usually has a potential space between the thrombus and the wall of the vessel, allowing the soft macrocoil mesh to passively slid between the surface of the thrombus and the vessel wall. It is to be noted that the deployed macrocoil mesh has no clearly defined shape (such as a basket, box, pyramidal coil complex, or the like) so that the macrocoil mesh may conform to any surface, such as that of the thrombus, as it passively surrounds that surface. Proximal ends of the controlling wires or strings may be used to control the location, deployment, tension, withdrawal and other movement of the macrocoil mesh by appropriately pushing, pulling, twisting, orienting, reorienting, positioning or otherwise moving those proximal ends. Passively encircling the clot reduces the chance of unwanted fragmentation of the thrombus and subsequent embolization of the fragment to vital tissues.

Where there is the deployment of two separate microcatheters, each with a separate macrocoil mesh element, each macrocoil mesh element may have separate end controls extending from each microcatheter, respectfully. Two mesh elements may integrate into a mass on the distal side of a thrombus. Push-pull guidance wire combinations are provided for the respective pairs of macrocoil elements.

In the use of a dual lumen catheter system deploying two macrocoil meshes with separate end controls for each mesh coming out of each lumen of the microcatheter, the distal ends of the mesh, the end controls may operate as push-pull wires, guidance wires, orientation elements, positioning elements, current carrying conductors (as when heating the microcoils in the macrocoil mesh) and the like. The end controls may be the same or different in the construction of the device to assure their ability to perform the ultimately desired tasks. Both end controls aid in the formation of a knot or tight tangle of the distal ends of each macrocoil mesh over the distal aspect of the thrombus, in the passive encirclement of the mid and proximal portions of the thrombus, and in the tightening of the meshwork around the surface of the thrombus.

It is to be noted that the dashed lines for catheters shown behind thrombus in some of the illustrations are not intended to limit the images to catheters passing through the thrombus, and in fact as clearly described herein, the location of the catheters is preferably adjacent to a thrombus. In this regard, it is one of the many novel aspects of the present technology that may be practiced according to these teachings that the catheters are intentionally passed adjacent to and not through a thrombus. It is also novel to pass multiple catheters adjacent to a thrombus in a single medical procedure according to the technology described herein There are numerous considerations of materials and properties that can be discussed herein to provide general and specific assistance to the design of instruments for various locations and procedures. The composition of the microcoils forming the macrocoil mesh may be any material that will retain its structural integrity during the expected length of an extended procedure, with safeguards built in for overextended periods of the coils being within an environment that may deteriorate or dissolve them. For example, if a standard procedure were expected to take 1-2 hours, it would be appropriate if the coils would remain intact in the operational environment for at least 24 hours and retain their physical properties. The microcoil material can be allowed to breakup or even dissolve after that time, in the event that there is a problem during the procedure, such as if a coil breaks or separates from the mesh.

Typically, the microcoil material will have essentially unaffected properties during the operation. Useful materials may be metals, alloys, plastics (polymeric materials), composites, ceramics and the like. The properties of the microcoil material are intended to provide the macrocoil mesh with resilient properties through the extensibility of the microcoils and macrocoils, and not necessarily elasticity in the material of the wire forming the various coils. The material of the wire may in fact be clearly inelastic within standards for metal wire, plastic wire, ceramic wire and composite wire, for example, having less than 20% or 10% elongation at breaking point for the wire.

Deployment of the at least one wire (with macrocoil mesh therein) may be from a single lumen on a catheter, multiple lumens on a single catheter, single lumens on multiple catheters, multiple lumens on multiple catheters, and 1, 2, 3, 4, 5 6 or more catheters or microcatheters may be used in the process.

The multiple coils may remain separate and distinct when deployed, may incidentally overlap, may intentionally overlap, may tangle with each other, may grip each other or otherwise interact. For example, when the distal ends of the macrocoils are extended from the microcatheter lumens (one microcatheter with two lumens or two separate microcatheters with one lumen each), they will overlap to produce a knot, tangle, or other firm connection. In addition, one or more of loops (the macrocoil loops) may engage each other to form a loose, incidental lock or slip resistant engagement between one or more macrocoils. Design may be built into the macrocoils, such as spikes (less preferred because of potential wall irritation), hooks and loops, posts, and hooks alone to produce a tighter mesh network and to decrease the likelihood of coil loops being extended to relatively ineffectual linearity when one end control is firmly pulled in attempting to position the mesh against the surface of a thrombus.

There are many other variants that may be provided in the practice of the present technology. Among the variations to be considered is the use of actual knot-tying techniques using multiple macrocoil/microcoil structures according to the present descriptions.

In the knot-tying format, two distinct macrocoils are fed from a single lumen, at least two separate lumens, or at least two adjacent lumens, such that a first macrocoil forms a loop with an opening large enough for a straight segment of a second macrocoil to pass through the opening, then passing at least one second macrocoil through the opening, and adjusting the local relative positions of the now at least two macrocoils so that a knot-like arrangement of the coils occurs. The interaction and engagement of the individual macrocoils of the at least two macrocoils also acts to provide a supporting structure and capability to the system.

This feature is more than superficially beneficial. When prior art capture systems are analyzed, they are found to be essentially one-size-fits-all, with only minimum variability in the size of the capture device allowed because of the more defined structure of the capture portion, as can be noted in Rosenbluth (U.S. Pat. No. 6,511,492), where a variety of cage and net structures are provided. Especially with the cage structures, the likelihood of a thrombus being disrupted during insertion and retraction is very high, especially with the more rigid elemental constructions in the pyramidal coil and cage structures. The relatively fixed size of the capture portion means that the system will use a single size for a large thrombus or a small thrombus. The potential for damage or inoperability varies among the range of size of the potential thrombus, and might require an attempt to provide distinct capture systems with advanced knowledge (which may be erroneous) of the specific size and shape of the thrombus. The present technology, because of the flexibility and conformability of the macrocoil/microcoil structure, can be used on an extremely wide variation in size of thrombi, and the coils will themselves conform to the size of whatever thrombus is present. The pull strings aid in altering the position of the distal tip of one or more macrocoils, so that the formation of the knot is facilitated. The pull string also tightens the mesh work distal to the thrombus. Finally, after macrocoils are passively looped around the mid and proximal aspects of the clot, the pull string aids in tightening the entire construct to decrease the chance of clot fragmentation.

The presently described technology includes a medical device for removing a thrombus from a blood vessel. The device may comprise at least one microcatheter lumen, the at least one microcatheter lumen having at least two regions of a deployable macrocoil therein, each macrocoil segment being capable of separate deployment along a length of the macrocoil, and each of the at least two deployable macrocoils, when deployed, being capable of being withdrawn from a location by withdrawal of the lumen. The device may have at least one macrocoil segment comprises a macrocoil thrombus engaging component having a length with a proximal end and a distal end, the length of the macrocoil segment comprised of microcoils that allow the length of the macrocoil segment to be extendable and flexible. The device may also have at least two macrocoil segments comprise a macrocoil thrombus engaging component having a length with a proximal end and a distal end, the length of the macrocoil segment comprised of microcoils that allow the length of the macrocoil segment to be extendable and flexible An alternative structure may comprise a medical device for removing a thrombus from a blood vessel having at least one microcatheter lumen, the at least one microcatheter lumen having at least one region of a distally positioned deployable macrocoil therein with respect to a length of the lumen and a shaped structure proximally positioned with respect to the length of the lumen. For example, the shaped structure may comprise a porous basket element, a porous coil of a different structure than the first macrocoil, a preformed shape or another porous deployable coil structure.

The present technology also includes, a method of capturing a solid object within a vessel in a patient comprising inserting a medical device for removing a solid object from a vessel, the device comprising at least one microcatheter lumen, the at least one microcatheter lumen having at least one region of a distally positioned deployable macrocoil therein with respect to a length of the lumen and a shaped structure proximally positioned with respect to the length of the lumen, the inserting done so that a first at least one deployable microcoil is beyond the solid object and the shaped structure is not beyond the solid object, deploying the first at least one deployable microcoil beyond the solid object to provide a distal engaging element beyond the solid object and deploying the shaped structure not beyond the solid object to form a proximal engaging structure for the solid object. In this method after forming the distal engaging structure and the proximal engaging structure, the device itself or portions thereof may be withdrawn to withdraw the solid object from the vessel or move the solid object within the vessel.

Another method of capturing a solid object within a vessel in a patient comprises inserting a medical device for removing a solid object from a vessel. The device would then comprise at least one microcatheter lumen, the at least one microcatheter lumen having at least two regions of a deployable macrocoil therein, each macrocoil segment being capable of separate deployment along a length of the macrocoil, and each of the at least two deployable macrocoils, when deployed, being capable of being withdrawn from a location by withdrawal of the lumen, the inserting being done so that a first at least one deployable microcoil is beyond the solid object and a second at least one other microcoil is not beyond the solid object, deploying the first at least one deployable microcoil beyond the solid object to provide a distal engaging element beyond the solid object and deploying the second at least one other microcoil not beyond the solid object to form a proximal engaging structure for the solid object. Also in this method, after forming the distal engaging structure and the proximal engaging structure, withdrawing the device or a portion thereof to withdraw the solid object from the vessel or move the solid object within the vessel while the solid object is secured distally and proximally along the direction of movement.

Additionally, as noted elsewhere, the conformability of the macrocoil system of the described technology offers the potential for reduced disruption of a thrombus and the generation of floating clots that could cause a stroke. Although there is never a guarantee of avoiding such issues during medical procedures, at least the potential is there for reducing the likelihood of such potentially disastrous events.

Animal and bench experiments have been performed using the Device. Studies were performed that investigated the removal of both soft and very firm fibrin-laden clot material from the arterial lumens of multiple blood vessels (renal, subclavian, external and internal carotid arteries) in the pig model. Soft clot was only a few hours old. Hard clot was made by allowing a pig's blood to stand for 4-6 days. The firm, fibrin-containing portion separated from the plasma, and the hard clot was embolized into the selected artery of a second pig.

Methodology Summary Study I

A commercially available microcatheter with an inner lumen of 0.018" was passed beyond the thrombus, specifically between the intima and the thrombus (non-occluded space between the thrombus and the walls). In the case of a firm thrombus, the process was aided by a commercially available 0.014" microguidewire. A thin nylon line (0.006") was attached to the distal end of a coil and the coil/string complex gently passed into a microcatheter to a point distal to the thrombus. Alternatively, the coil/string complex was preloaded into the microcatheter that was passed without the aid of a microguidewire past the distal end of the thrombus. The coils were pushed from the microcatheter, which was progressively pulled back until it was proximal to the thrombus and clot extraction attempted, as previously described.

Conclusions Summary Study I

Soft clot tended to be removed easily from the arteries studied because the clot adhered to the meshwork of the coil and the pulling wire of the Device. However, initial experiments with single coils of different sizes, including both 3-D and 2-D coils, demonstrated the inability to consistently and successfully extract the firm clot with this method, even when the coil had formed a mesh around the thrombus and the nylon string was pulled as much as possible to tighten the mesh around the clot. Rather, the coil sometimes simply unraveled from around the thrombus, sliding back into the more proximal microcatheter. It was apparent in those failed circumstances that the loops of the coil were simply wrapping around the clot without becoming tightly engaged and that such a non-structured mesh was insufficient to overcome the combination of forces keeping the thrombus in place, including friction between the thrombus and the intima and blood flow pushing the embolus distally. However, intertwining and/or overlapping of the loops along the distal aspect of the thrombus, as one would tie a shoelace, kept the distal mesh in place without allowing the entire coil complex to unravel.

Methodology Summary Study II

In subsequent experiments, two microcatheters were passed distal to the firm clot, each positioned in the same manner as previously described. The distal end of a 3-D coil was pushed into the arterial lumen from the first microcatheter, then the distal end of a second coil. Either a 2-D or a 3-D configuration was pushed forward from the second microcatheter, allowing loops of the two coils to intertwine. By "two coils" in this description, it is meant that there are two masses of coils, each delivered from a microcatheter. The term includes two coil masses emanating from two lumens of a single microcatheter, as opposed to requiring two distinct microcatheters. Further coils were extended to make a complex, random mesh, and then the nylon strings were pulled so that a tight "cap" or "knot" was formed on the distal surface of the clot. The microcatheters were partially withdrawn and as more coils were pushed from the microcatheter, they passively encircled the middle portions of the clot. The process was continued with more coils (at least a total of two and up to six coils would be used in a preferred range of mesh applications) placed proximal to the clot. The nylon strings were then pulled tightly to form a tight meshwork encircling the entire clot so that little or no fragmentation would occur.

Conclusions Summary Study II

Using this technique, it was possible to successfully extract firm clots from all arteries embolized without evidence of fragmentation on subsequent post-extraction angiography. Coils having diameters equal to or slightly larger than that of the arterial lumen appeared to make the best distal meshwork and therefore, the most stable macrocoil constructs. By then passively encircling the clot, there was no tendency for the distal "cap" to slide from the top over the side of the clot. Post-extraction angiography and post-mortem examination, including microscopy, did not demonstrate any evidence of arterial injury.

Other variations in the materials, designs and processes may be apparent and obvious to those skilled in the art from the generic teaching and examples provided herein.

What is claimed:

1. A device for retrieval of objects from within vessels of patients comprising: a length of microcoil having approximately helical turns continuously or within adjacent sections of the length of microcoil and the helical turns have an average diameter, at least some of the continuous length or the segments in the length of microcoil having eyelets that extend beyond the average diameter, and a core wire passing through at least some adjacent eyelets from a distal end to a proximal end of the length of microcoil, the core wire being restrained near the distal end of the length of microcoil.

2. The device of claim 1 wherein the average diameter of the helical turns is less than 0.050 inches.

3. The device of claim 2 carried within a lumen of a microcatheter wherein the lumen internal diameter is greater than the average diameter of the helical turns of the length of microcoil.

4. The device of claim 2 wherein tension applied on the proximal end of the core wire will cause the length of microcoil to form loops outside of the average diameter of the length of microcoil.

5. A device for insertion into a vessel for the removal of at least one solid object from within the vessel, the device comprising: a catheter having a lumen; within the lumen of the catheter is at least: a macrocoil elongate element having an axis and a length, multiple eyelets on the macrocoil elongate element that extend away from the axis, and a core wire extending through at least two of the multiple eyelets; wherein the core wire is attached at a distal point along the length of the macrocoil, wherein increasing tension on the core wire, which tension is in part guided by the core wire passing through multiple eyelets, causes the macrocoil to form loops, curves, bundles or a non-linear compressed shape.

6. The device of claim 5 wherein the macrocoil element consists of a continuous length of microcoils or segments of microcoils along the length of the macrocoil that add flexibility and conformability to the microcoil.

7. The device of claim 6 wherein the macrocoil element comprises a continuous length of microcoils.

8. The device of claim 7 wherein eyelets are formed along the length of the macrocoil element by dislocated microcoils extending away from the axis of the macrocoil elongate element and providing openings through which the core wire may pass.

9. The device of claim 6 wherein microcoils are positioned within the macrocoil so that an exterior surface of the microcoils positioned against a thrombus in a vessel will first engage an exterior surface of the thrombus.

10. The device of claim 5 wherein when tension is applied to the core wire, the macrocoil forms loops along the length of the macrocoil.

11. The device of claim 10 wherein at least some loops will be formed adjacent at least one eyelet.

12. A medical device for removing a thrombus from a blood vessel, comprising at least one microcatheter lumen, the medical device comprising at least one elongated flexible element lumen comprising a) at least one macrocoil comprising a continuous segment of microcoils or b) at least two separate flexible element segments comprising microcoils therein, each segment of the at least one macrocoil being capable of conformation to at least one solid object after deployment from the microcatheter lumen, each segment of flexible elements having eyelets extending away from an axis of the flexible element and a core wire extending through the eyelets, wherein tension on the core wire causes at least some adjacent eyelets to contract, forming a loop in the flexible element, the flexible element, when deployed to a location outside of the microcatheter lumen, is capable of being withdrawn from the location by withdrawal of the microcatheter lumen.

13. The medical device of claim 12 wherein the flexible element consists essentially of a continuous set of microcoils having an axis, the core wire and at least some eyelets are formed by microcoils extending away from the axis.

14. The medical device of claim 12 wherein eyelets are formed on the macrocoil by affixed eyelets extending away from the axis.

15. The medical device of claim 12 wherein the core wire is secured to at least some eyelets.

16. A medical device for removing a thrombus from a blood vessel, comprising at least one microcatheter lumen, the at least one microcatheter lumen having at least one deployable flexible element comprising a macrocoil having sections of microcoils separated by offset microcoils that form eyelets, each section of microcoils being capable of conformation to at least one solid object after deployment from the microcatheter lumen, each eyelet extending away from an axis of the microcoils with a core wire extending through the eyelets, wherein tension on the core wire causes at least some adjacent eyelets to contract towards each other, forming a loop in the flexible element, the loop comprising microcoils, and each of the at least one deployable flexible elements, when deployed to a location outside of the microcatheter lumen, is capable of being withdrawn from the location by withdrawal of the lumen.

17. The medical device of claim 16 wherein the flexible element consists essentially of a continuous set of microcoils having an axis, the core wire and at least some eyelets are formed by microcoils extending away from the axis.

18. The medical device of claim 16 wherein eyelets are form on the macrocoil by affixed eyelets extending away from the axis.

19. The medical device of claim 16 wherein the core wire is secured to at least some eyelets.

20. The device of claim 16 wherein microcoils are positioned within the macrocoil so that an exterior surface of the microcoils positioned against the thrombus in the blood vessel will first engage an exterior surface of the thrombus when the loop is drawn against the thrombus.

* * * * *